US010946165B2

(12) United States Patent
Metzger

(10) Patent No.: US 10,946,165 B2
(45) Date of Patent: Mar. 16, 2021

(54) MODULATION OF BRAINWAVE ACTIVITY USING NON-INVASIVE STIMULATION OF SENSORY PATHWAYS

(71) Applicant: Phoenix NeuroStim Therapeutics, LLC, Providence, RI (US)

(72) Inventor: Steven Metzger, Providence, RI (US)

(73) Assignee: Phoenix NeuroStim Therapeutics, LLC, Providence, RI (US)

( * ) Notice: Subject to any disclaimer, the term of this patent is extended or adjusted under 35 U.S.C. 154(b) by 379 days.

(21) Appl. No.: 15/571,583

(22) PCT Filed: May 4, 2016

(86) PCT No.: PCT/US2016/030707
§ 371 (c)(1),
(2) Date: Nov. 3, 2017

(87) PCT Pub. No.: WO2016/179240
PCT Pub. Date: Nov. 10, 2016

(65) Prior Publication Data
US 2018/0221620 A1 Aug. 9, 2018

Related U.S. Application Data

(60) Provisional application No. 62/156,715, filed on May 4, 2015.

(51) Int. Cl.
*A61M 21/02* (2006.01)
*A61N 1/04* (2006.01)
(Continued)

(52) U.S. Cl.
CPC .......... *A61M 21/02* (2013.01); *A61B 5/0478* (2013.01); *A61B 5/04842* (2013.01);
(Continued)

(58) Field of Classification Search
CPC .......... A61M 21/00–02; A61B 5/4064; A61B 5/6803; A61B 5/6814; A61N 1/0456
See application file for complete search history.

(56) References Cited

U.S. PATENT DOCUMENTS

| 8,190,263 B2 | 5/2012 | Machado et al. |
| 8,369,995 B2 | 2/2013 | Nanami |

(Continued)

FOREIGN PATENT DOCUMENTS

| DE | 10 2012 002 436 A1 | 8/2013 |
| EP | 2801389 A1 | 11/2014 |

(Continued)

OTHER PUBLICATIONS

International Search Report and Written Opinion for International Application No. PCT/US2016/030707 dated Jul. 6, 2016.

(Continued)

*Primary Examiner* — Thaddeus B Cox
(74) *Attorney, Agent, or Firm* — Wolf, Greenfield & Sacks, P.C.

(57) ABSTRACT

Methods and apparatus for modulation of the central nervous system, and more particularly for modulation of brain oscillatory activity and the brain networks that give rise to it. The methods involve using one or more non-invasive stimuli, either alone or in combination, to increase, decrease, or otherwise modulate neural oscillations in the brain. Also described are methods and devices for detecting sub-optimal or pathological neural oscillatory patterns, developing treatment protocols to modify the neural oscillations in a desired manner, introducing a non-invasive stimulus or stimuli through one or more sensory pathways to treat the conditions, and adjusting the treatment protocol to improve the therapeutic effect of the stimulus or stimuli.

39 Claims, 8 Drawing Sheets

(51) Int. Cl.
*A61M 21/00* (2006.01)
*A61N 1/36* (2006.01)
*A61B 5/0484* (2006.01)
*A61B 5/00* (2006.01)
*A61B 5/0478* (2006.01)
*A61B 5/16* (2006.01)

(52) U.S. Cl.
CPC .......... *A61B 5/04845* (2013.01); *A61B 5/168* (2013.01); *A61B 5/4064* (2013.01); *A61B 5/6803* (2013.01); *A61B 5/6814* (2013.01); *A61N 1/0456* (2013.01); *A61N 1/0484* (2013.01); *A61N 1/36025* (2013.01); *A61B 2562/0209* (2013.01); *A61M 2021/005* (2013.01); *A61M 2021/0022* (2013.01); *A61M 2021/0027* (2013.01); *A61M 2021/0072* (2013.01); *A61M 2230/10* (2013.01)

(56) References Cited

U.S. PATENT DOCUMENTS

| | | | |
|---|---|---|---|
| 8,380,316 | B2 | 2/2013 | Hagedorn et al. |
| 8,494,627 | B2 | 7/2013 | Bikson et al. |
| 10,625,042 | B2 | 4/2020 | Metzger |
| 2004/0116978 | A1 | 6/2004 | Bradley |
| 2004/0173220 | A1 | 9/2004 | Harry et al. |
| 2007/0043268 | A1 | 2/2007 | Russell |
| 2007/0043401 | A1 | 2/2007 | John |
| 2007/0142874 | A1 | 6/2007 | John |
| 2008/0177352 | A1 | 7/2008 | Pascual-Leone et al. |
| 2010/0048985 | A1 | 2/2010 | Henke et al. |
| 2011/0029044 | A1 | 2/2011 | Hyde et al. |
| 2012/0310298 | A1 | 12/2012 | Besio et al. |
| 2013/0066137 | A1 | 3/2013 | Hulvershorn |
| 2014/0057232 | A1* | 2/2014 | Wetmore ............ A61B 5/0036 434/236 |
| 2015/0066104 | A1* | 3/2015 | Wingeier ............ A61B 5/4836 607/45 |
| 2015/0088224 | A1* | 3/2015 | Goldwasser ....... A61N 1/36082 607/45 |
| 2015/0174418 | A1* | 6/2015 | Tyler ..................... A61B 5/055 601/2 |
| 2016/0279380 | A1 | 9/2016 | Metzger |

FOREIGN PATENT DOCUMENTS

WO    WO 2007/138598 A2    12/2007
WO    WO 2013/192582 A1    12/2013

OTHER PUBLICATIONS

Extended European Search Report for European Application No. EP 14859074.8 dated Jul. 24, 2017.
International Search Report and Written Opinion for International Application No. PCT/US2014/63827 dated Feb. 13, 2015.
International Preliminary Report on Patentability for International Application No. PCT/US2014/63827 dated May 19, 2016.
McIntosh, Contexts and catalysts: a resolution of the localization and integration of function in the brain. Neuroinformatics. 2004;2:175-81.
Sakowitz et al., Oscillatory frontal theta responses are increased upon bisensory stimulation. Clinical Neurophysiology. 2000;111:884-93.

\* cited by examiner

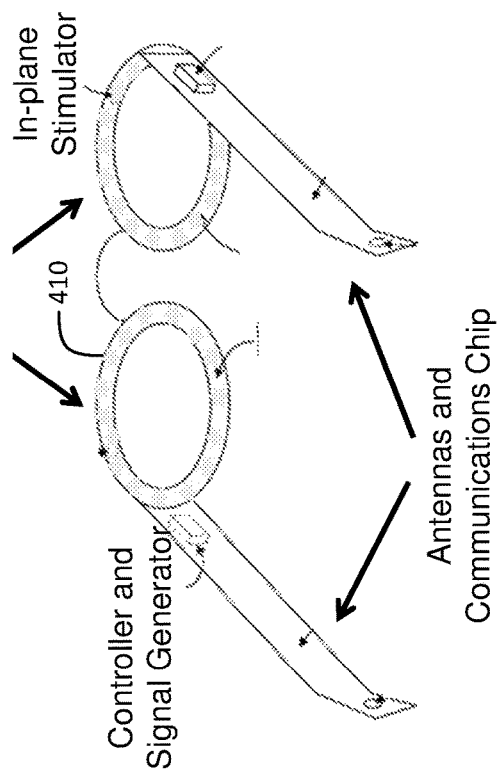 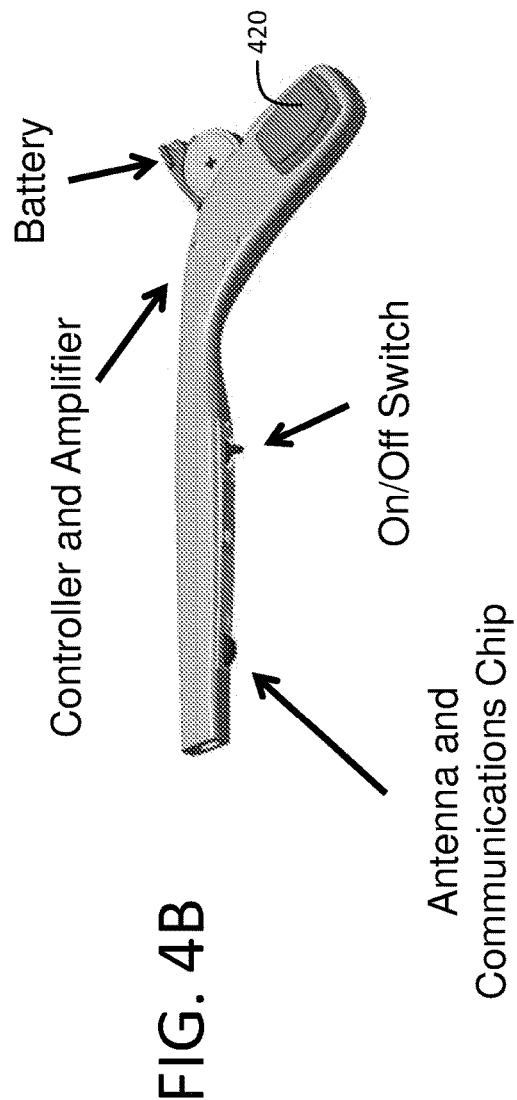
FIG. 4A
FIG. 4B

MODULATION OF BRAINWAVE ACTIVITY USING NON-INVASIVE STIMULATION OF SENSORY PATHWAYS

RELATED APPLICATIONS

This application is a National Stage application of PCT/US2016/030707, filed on May 4, 2016 which claims priority under 35 U.S.C. § 119(e) to U.S. Provisional Application Ser. No. 62/156,715, entitled "MODULATION OF BRAINWAVE ACTIVITY USING NON-INVASIVE STIMULATION OF SENSORY PATHWAYS" filed on May 4, 2015, each of which is herein incorporated by reference in its entirety.

BACKGROUND

The brain is estimated to contain over 100 billion neurons and almost 1 trillion connecting synapses. To harness the amazing processing capabilities that this population gives rise to, the brain relies on communication both within and between a large and diverse group of specialized structures. Brain regions are connected through the mechanism of synchronized neural oscillation—the rhythmic and/or repetitive electrical activity generated spontaneously and in response to stimuli by neural tissue. Functionally, neural oscillations are a prominent feature of brain activity. The synchronization of these oscillations, which reflects the temporally precise interaction of neural assemblies, is the putative mechanism whereby brain regions subserving specific functions communicate with each other in order to accomplish perception, cognition, and action.

Neural oscillations, often colloquially referred to as "brainwaves," are, by convention, divided into five frequency bands, shown in the table below. Brainwaves in each of these frequency bands is believed to play distinct roles in normal brain function and may be the underlying cause of some neurological conditions.

| Frequency Bands for Neural Oscillations | |
| --- | --- |
| Frequency Band Name (Symbol) | Frequency Range |
| Delta (δ) | <4 Hz |
| Theta (θ) | 4 Hz-8 Hz |
| Alpha (α) | 8 Hz-13 Hz |
| Beta (β) | 13 Hz-35 Hz |
| Gamma (γ) | 35 Hz-200 Hz |

The role of brainwaves as essential building blocks in sensory-cognitive processes has become a central tenant of modern neuroscience. Research has shown that even simple sensory, motor, and cognitive tasks often depend on the precise coordination of multiple brain areas. The brain's dependency on neural oscillation and synchrony has led to the belief that some neurological conditions are caused by the brain's inability to communicate internally effectively. For example, clinical studies have shown that event-related oscillations in different frequency bands are modified throughout the cortex in pathologic brains, and particularly so in patients with cognitive impairments such as schizophrenia, autism, epilepsy, bipolar disorder, and attention deficit disorder (ADD). Abnormal communication between neural assemblies is also believed to contribute to motor symptoms manifest in neurological conditions, such as the presence of tremor and poverty of movement in Parkinson's disease.

Commonly, patients with these and similar conditions are initially treated with medication. While a large proportion of these patients may be aided by pharmaceutical interventions, many are not helped by medication, or are not helped sufficiently to provide the desired levels of relieve. For patients in which treatment with pharmaceutical intervention is not satisfactory, invasive treatments, such as Deep Brain Stimulation (DBS), which involves the implantation of stimulation electrodes directly into brain tissue to modulate brain activity in particular regions, are often recommended.

SUMMARY

Some embodiments are directed to a system for providing neuromodulation to treat a patient having a central nervous system condition using one or more sensory stimuli. The system may comprise one or more processors programmed with instructions to implement a treatment plan by providing neuromodulation parameters to one or more sensory stimulators. The system may also receive sensor input from one or more sensors configured to measure neural activity in brain regions and/or brain networks being modulated in response to presentation of the sensory stimuli. The one or more processors may be programmed to interpret the received sensor input relative to baseline and/or historical measurements to adjust one or more of the stimulation parameters to provide effective treatment to the patient.

In some embodiments, at least one of the stimuli provided to the patient using a brainwave neuromodulation device (BND) is a bandwidth-limited stochastic stimulus configured to selectively modulate neural activity within a specific brainwave frequency band or bands. In some embodiments the BND is designed to provide sensory stimulation via at least two sensory pathways as part of a neurostimulation protocol.

Some embodiments are directed to a configurable, portable, and/or wearable brain neuromodulation device (BND) that enables neuromodulation therapy to be performed outside of a traditional clinical or research setting. In some embodiments, the BND may be adoptable for everyday use by the patient during performance of everyday activities including, but not limited to, reading, driving, sleeping, and engaging in learning activities in a classroom.

In some embodiments, one or more stimulators and/or sensors are integrated with processing circuitry to provide a BND capable of modulating brain activity in response to real-time data feedback. BNDs for use with some embodiments may include a programming interface that enables the processing circuitry of the device to be programmed by a medical practitioner, a patient, or any other authorized user. In some embodiments, programming instructions may be downloaded to the BND locally by connecting the device to a computer and/or the BND may be programmed remotely via one or more networks (e.g., the Internet) using any suitable programming interface.

Some embodiments are directed to a method of defining a neuromodulation protocol that, for a given combination of brain region and brainwave frequency band, can maximize a neuromodulatory effect of a stimulus by presenting the stimulus via specific sensory pathways. In some embodiments, the sensory stimulus may be "steered" to provide optimal neuromodulation of specific brain networks to provide effective therapy for patients with central nervous system conditions including, but not limited to, ADHD, ADD, dyslexia, autism, Asperger's Syndrome, bipolar disorder, schizophrenia, and Parkinson's disease.

Some embodiments are directed to a non-transitory computer readable medium encoded with a plurality of instructions that, when executed by at least one computer processor, perform a method of modulating one or more brain regions using one or more sensory stimuli presented through a sensory pathway. As used herein, the terms "sensory stimuli" and "sensory stimulus" refer to any stimulus presented via a sensory pathway regardless of actual form of the stimulus. Examples of sensory stimuli include, but are not limited to, auditory stimuli, visual stimuli, tactile stimuli, electrical stimuli, mechanical stimuli, magnetic stimuli, or some combination thereof. For example, a stimulus may be provided via the auditory pathway using sound waves, electrical stimulation, mechanical stimulation, or using a stimulus have any other form capable of stimulating the auditory pathway.

Some embodiments are directed to a neuromodulation system capable of providing both reinforcing and inhibitory modulation effects on brainwave activity in target brain regions. Some embodiments use stochastic resonance to degrade or inhibit brainwave activity in particular brain regions. Some embodiments are configured to incrementally increase or decrease brainwave activity to closely resemble the natural cycling of brainwave activity.

It should be appreciated that all combinations of the foregoing concepts and additional concepts discussed in greater detail below (provided that such concepts are not mutually inconsistent) are contemplated as being part of the inventive subject matter disclosed herein.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 4A and 4B illustrate portions of a multimodal device that may be used as a BND in accordance with some embodiments;

DETAILED DESCRIPTION

Figure 1:
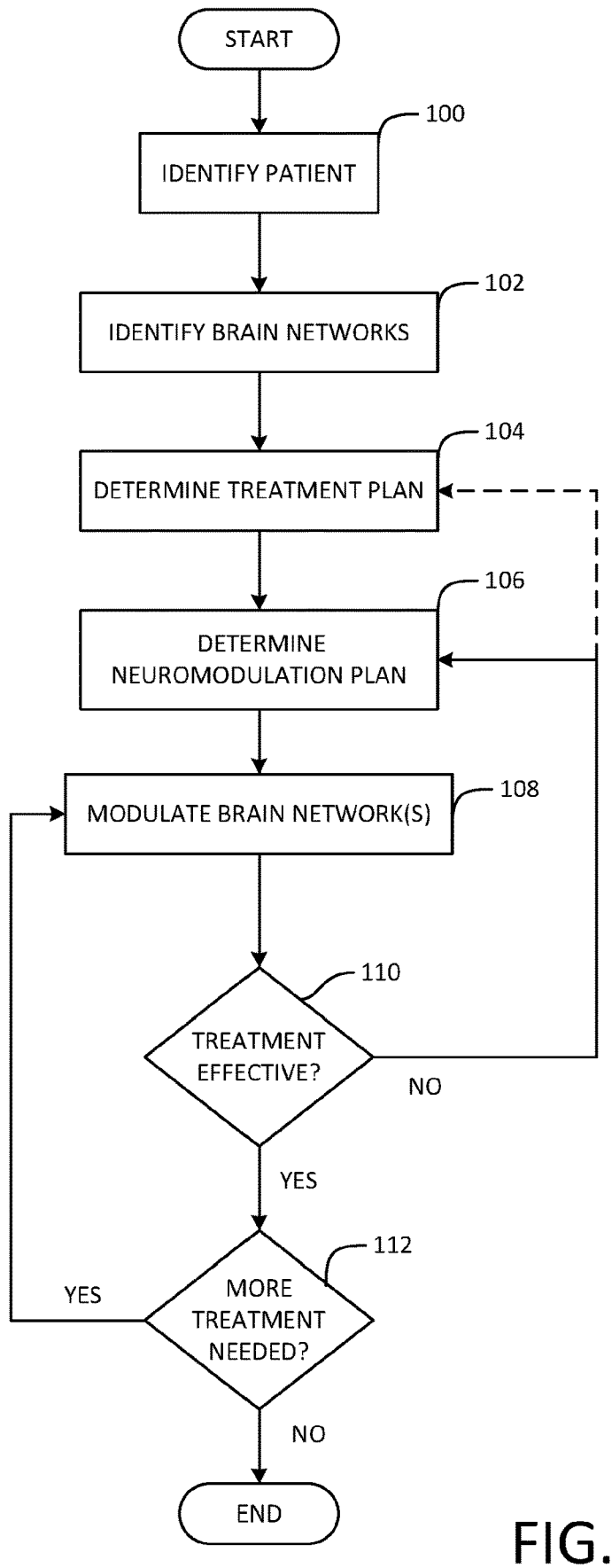
FIG. 1 is flowchart of a process for modulating one or more brain networks to provide treatment for a central nervous system condition in accordance with some embodiments.

Some conventional techniques for treating central nervous system conditions are associated with risks that limit their use in widespread populations. For example, Deep Brain Stimulation introduces significant risks associated with open cranial surgery and the risk of damage to areas of the brain adjacent to the insertion route of the stimulation electrodes. Furthermore, the electrical stimulus applied by the DBS devices may damage surrounding brain tissue, even in distal areas of the brain connected to the site of stimulation. Additionally, the effectiveness of pharmaceutical intervention to treat central nervous system conditions varies substantially among patients and across different diseases, and such interventions are often targeted at addressing the symptoms of the condition rather than focusing on remediating the dysfunction of the underlying brain networks.

More recently, several less invasive neurostimulation technologies have become available. These technologies, most notably transcranial magnetic stimulation (TMS) and transcranial electric stimulation (TES), have shown some efficacy in treating tinnitus, migraines, depression, and epilepsy. However, the observed therapeutic effects of these treatments have generally not persisted for significant periods of time beyond the treatment window. Additionally, because of safety concerns and other reasons, use of these technologies is generally not administered outside of a clinical or research setting, and the long-term benefit of these technologies remains unknown.

The inventor has recognized and appreciated that conventional techniques for treating central nervous system conditions can be improved through targeted stimulation of underlying cortical networks in locations and frequency bands with abnormal brain activity using non-invasive sensory stimuli. Projections from the primary auditory, visual, and somatosensory cortices reach throughout the brain, reflecting their importance to the performance of cognitive and motor functions. Further, neuroimaging studies have demonstrated that sensory stimuli have a profound effect on the excitation of diverse regions within the brain well beyond the specialized cortical structures that initially receive such stimuli.

Auditory, visual, and somatosensory pathways may preferentially stimulate different cortical regions and give rise to synchronized neural oscillations between the stimulated cortices and other structures within the brain. To this end, some embodiments are directed to using sensory stimuli designed to stimulate particular neural oscillations within the central nervous system to modulate (e.g., increase or decrease) neuronal activity in brain regions to improve the functioning of brain networks in patients with central nervous system conditions. An illustrative example of treating Attention Deficit Hyperactivity Disorder (ADHD) using techniques in accordance with some embodiments is described in detail below. However, it should be appreciated that the techniques described herein for treating central nervous system conditions is not limited for use with ADHD patients, but is also applicable to treating any other central nervous system condition associated with an unwanted state of neuronal oscillations in the brain including, but not limited to, autism, dyslexia, epilepsy, schizophrenia, bipolar disease, loss of function due to stroke or injury, and Parkinson's disease. For example, some embodiments are suitable for providing treatment to individuals associated with a condition related to normal aging, learning or re-learning a motor skill, providing cognitive enhancement, and any other suitable type of condition.

FIG. 1 shows an illustrative process comprising a plurality of acts for modulating neuronal activity in brain networks to treat central nervous system conditions in accordance with some embodiments. In act 100, a patient is identified as having a central nervous system condition that is appropriate for treatment using one or more of the techniques for brain modulation described herein. Patients may be identified in any suitable way, examples of which are discussed in more detail below. After a patient is identified, the process proceeds to act 102, where one or more brain networks underlying the central nervous system condition are identified. In some embodiments, the brain network(s) may be identified based, at least in part, on population data determined for patients having the same central nervous system condition and/or a same or similar behavioral, psychological, or neurological profile as the patient. In other embodiments, the brain network(s) may be identified based at least in part, on patient-specific data including, but not limited to, results from behavioral and/or neuropsychological testing or functional neuroimaging. In yet further embodiments, the brain network(s) may be identified based, at least in part, on a combination of population data and patient-specific data.

After identifying the brain network(s) underlying the central nervous system condition, the process proceeds to act 104, where a treatment plan for the patient is determined. The treatment plan may describe one or more objectives for treatment, such as bringing neuronal oscillations for a particular brain region to within a normal range or enabling the patient to perform within normal limits on one or more tasks. After the treatment plan is determined, the process proceeds to act 106, where a neuromodulation plan is determined based on the treatment plan to accomplish or facilitate accomplishment of one or more of the objectives of the treatment plan. In some embodiments, one or more other patient actions (e.g., behavioral modification, diet, exercise, etc.) may be used in addition to a neuromodulation plan to accomplish one or more of the objectives of the treatment plan, and aspects of the invention are not limited in this respect.

After determining a neuromodulation plan, the process proceeds to act 108, where the identified brain network(s) are modulated in accordance with the determined neuromodulation plan. For example, one or more sensory stimuli adapted to provide appropriate neuromodulation within a particular frequency band or bands may be presented to the patient continuously, at suitable intervals, or when the patient is performing a particular task (e.g., reading, counting, singing, etc.), as prescribed in the treatment plan. In some embodiments, neuromodulation may be presented to the patient using one or more devices that are portable or wearable such that the neuromodulation may be provided to the patient outside of a clinical setting. Any type or combination of sensory stimuli may be presented to the patient for treating the central nervous system condition of the patient, non-limiting examples of which are discussed in more detail below.

Following modulation of the brain network(s), the process proceeds to act 110, where the efficacy of the brain network modulation with respect to the treatment objectives is evaluated. The efficacy of the brain network modulation may be determined in any suitable way. For example, functional neuroimaging data (e.g., EEG data) following neuromodulation may be collected and compared to baseline neuroimaging data for the patient and/or population neuroimaging data (e.g., for patients without the central nervous system condition or patients for which neuromodulation has been successful in remediating the central nervous system condition). Rather than comparing neuroimaging data directly, one or more measures determined from the neuroimaging data may be compared pre- and post-neuromodulation, as discussed in more detail. Additionally, in some embodiments, other measures separate from neuroimaging data may be compared to evaluate the effectiveness of the neuromodulation. For example, performance on one or more behavioral, cognitive, or neurological tests pre- and post-neuromodulation may be compared to determine the effectiveness of the neuromodulation treatment. Any combination of neuroimaging measures and non-neuroimaging measures may also be used to assess the efficacy of neuromodulation treatment, and aspects of the invention are not limited in this respect.

In some embodiments, the effectiveness of the treatment may be determined by comparing current post-neuromodulation measurements to one or more previous post-neuromodulation measurements to evaluate whether a change in the measurements over time indicates that the patient's condition is improving, worsening, or staying the same as a result of the neuromodulation treatment.

If it is determined in act 110 that the neuromodulation treatment was effective, the process proceeds to act 112, where it is determined whether additional treatment is needed. The determination of whether additional treatment is needed may be made using any suitable criterion or criteria in accordance with the treatment plan for the patient. For example, if it is determined in act 110 that one or more post-neuromodulation tests are within a normal range, it may be determined that further treatment is not needed and the process ends. Alternatively, if the neuromodulation treatment improved the condition of the patient, but one or more post-neuromodulation tests are still outside a normal range, it may be determined in act 112 to continue treatment with the same neuromodulation protocol in an effort to further improve the patient's condition. If it is determined that additional treatment is needed, the process returns to act 108, where brain network(s) of the patient are further modulated in accordance with the neuromodulation plan. The process then repeats until it is determined in act 112 that treatment is no longer needed or until it is determined in act 110 that the treatment is no longer effective.

If it is determined in act 110 that the neuromodulation treatment was not effective, the process returns to act 106 to modify the neuromodulation plan based, at least in part, on information obtained in determining whether the treatment was effective in act 110. For example, one or more neurostimulation parameters may be modified to improve the efficacy of the neuromodulation treatment. Optionally, based on the information obtained in determining whether the treatment was effective, the process may return to act 104 where the treatment plan may be modified. For example, after providing one or more sessions of neuromodulation therapy, if the patient's condition is not improving, one or more aspects of a treatment protocol (e.g., the treatment objectives) may be modified based at, least in part, on sensed data, patient outcomes, network interactions, any other information obtained in determining that the treatment was not effective, or any combination thereof.

In an example of modifying a treatment protocol, it may be determined that the treatment protocol specified modulation of brainwave activity in one or more brain regions of a targeted brain network that produced unwanted brainwave activity in a related brain network, thereby interfering with the intended outcome of the treatment protocol. To correct for the unwanted brainwave activity, the treatment protocol may be modified by specifying one or more different brain regions of the targeted brain network for modulation. Alternatively, the treatment protocol may be modified to specify modulation of the connecting network that, in combination with modulation of the targeted brain network, may achieve the objectives of the treatment protocol.

In another example, brainwave activity in frequency bands, brain networks, and/or brain regions not considered in the original treatment plan may be examined to determine if unwanted brainwave activity in these areas influenced the outcomes of the failed treatment protocol. For example, unwanted coupling between brain regions may occur in response to changes in brainwave activity occurring in previously unrelated brain regions or brain networks. Accordingly, the original treatment protocol may have modulated one or more unrelated networks or regions in a manner that interfered with the treatment outcomes of the treatment plan, and the treatment protocol may be modified by specifying a new treatment protocol that addresses this unwanted brainwave activity.

Having provided an overview of the acts of the illustrative process of FIG. 1, additional details of exemplary implementations of each of these acts is described in further detail below.

As discussed above, in act 100, patients may be identified in any suitable way, and embodiments are not limited in this respect. In some implementations, patient identification may be based on criteria selected by medical practitioners providing treatment. For example, patients may be selected based on medical history, psychological or neurological testing, neuroimaging data (e.g., structural and/or functional neuroimaging data), or using any other suitable criteria. To determine whether a patient is appropriate for treatment using neuromodulation, patients who demonstrate certain profiles of test results may be compared to profiles of other patients who responded well, or did not respond well, to neuromodulation treatment. In some embodiments for treating patients with ADHD, a combination of psychological testing and functional neuroimaging may be used to identify appropriate patients for treatment, as discussed in more detail below.

ADHD is a heterogeneous diagnosis encompassing a broad range of developmental, cognitive and behavioral pathologies. Between nine and eleven percent of children between the ages of 4-17 are believed to suffer from ADHD, and these adolescents often exhibit multiple symptoms including hyperactivity, impulsivity and inattention. The Diagnostic and Statistical Manual (DSM) of the American Psychiatric Association has recognized as many as nine different diagnoses that have been grouped, ungrouped and regrouped in successive versions of the manual. The current version of the manual (DSM-IV-TR) identifies three subtypes of ADHD patients which are: 1) predominantly hyperactive; 2) predominantly inattentive and 3) combined.

The classification rules of DSM-IV-TR require that the patient exhibit at least four symptoms of hyperactivity-impulsivity to be diagnosed as predominantly hyperactive and six symptoms of inattention to be classified as predominantly inattentive. Reflecting the multifaceted presentation of ADHD, there are a large number of psychometric and skill-based testing methodologies that are commonly used in diagnosing ADHD. The most generally accepted and widely uses tests are: The Attention Deficit Hyperactivity Rating Scale-IV (ADHD-IV), Connors' Rating Scales revised (CRS-R), Conners' Continuous Performance Test (CPT), Mood Disorder Questionnaire, Attentional Capture Test, and Wide Range Assessment Test-4 (WRAT-4).

To identify a patient as meeting the threshold for diagnosis with ADHD, a clinical evaluation of a patient may be performed. For example, an examination by a trained psychiatrist, cognitive and behavioral testing using one or more of the tests described above, and observational reports from parents and teachers may be considered to determine whether a patient meets the threshold for diagnosis with ADHD.

If it is determined that the patient meets the threshold for diagnosis with ADHD, in some embodiments, further testing may be performed to determine whether the patient is a suitable candidate for neuromodulation therapy using one or more of the techniques described herein. In some embodiments, the further testing may include performing one or more functional neuroimaging procedures on the patient to determine whether the patient demonstrates abnormal brain activation patterns. In one implementation, patients diagnosed with ADHD may be evaluated using quantitative electroencephalography (QEEG). For example, one or more EEG electrodes may be placed on the scalp of the patient in a suitable configuration (e.g., a standard 10-20 electrode placement) and EEG may be recorded during an Eyes Open-Resting State (EO-RS) condition and/or while the patient is performing a suitable task including, but not limited to, an emotional task, a sensory task, a memory task, a stressor task, a cognitive task, and a target detection task. The results of the QEEG exam may be processed using known techniques to remove any artifacts and other extraneous from the data relevant to the patient's brainwave activity. The processed EEG signals, representing a baseline QEEG state for the patient, may then be used to evaluate whether the patient is a suitable candidate for neuromodulation therapy using one or more of the techniques described herein.

A brainwave abnormality often identified in the EEG patterns of patient with ADHD compared to patients without ADHD is an elevated ratio of theta brainwave activity to beta brainwave activity (hereinafter referred to as "TBR") as measured at the Cz EEG electrode. For example, a meta-analysis of studies investigating TBR in ADHD patients found that a substantial subgroup of patients with ADHD had an elevated TBR compared to patients without ADHD, and that having a TBR greater than 7.5 was confirmatory of an ADHD diagnosis. Accordingly, in some embodiments, one or more EEG measurements (e.g., TBR measured at the Cz electrode) may be compared to a threshold value (e.g., 7.5) to determine whether the patient is a suitable candidate for neuromodulation therapy. If a comparison of the EEG measurement(s) with the threshold value indicates that the patient may not be a suitable candidate for neuromodulation therapy (e.g., if the TBR is less than 7.5) one or more additional tests may be performed to determine whether the patient is a suitable candidate for neuromodulation therapy. For example, the patient may be evaluated using a Neuro-psychiatric Interpretive EEG-based Assessment Aid (NIEA), such as the NEBA® system available from Neba Health, Augusta, Ga. The NEBA® system uses algorithms that take into consideration the patient's age and other factors that may influence the interpretation of EEG data. If the output of the NIEA confirms the ADHD diagnosis, the patient may be determined to be suitable for neuromodulation therapy in accordance with the techniques described herein.

The identification of underlying brain network(s) in act 102 may be determined in any suitable way. For example, the underlying brain network(s) may be determined based, at least in part, on population data for patients having a same or similar central nervous system condition as the patient. Examples of population data include, but are not limited to, data based on anatomical studies of animal or post-mortem brains, structural imaging data, including computerized tomography (CT), magnetic resonance imaging (MRI) and its variants including functional MRI (fMRI), blood oxygenation level dependent (BOLD) imaging, and diffusion tensor imaging (DTI). Functional imaging techniques accomplished with external sensors using techniques that include pharmaceutical manipulations may also be used to identify brain network(s), as such techniques may also provide information related to the metabolism, activity, connectivity, and neurochemistry of brain networks. Any combination of this population data, including use of a single type of population data, may be used to identify one or more brain networks for modulation in accordance with the techniques described herein.

Appreciating that some central nervous system conditions present with variable symptoms that may involve different brain networks from patient to patient, some embodiments identify brain network(s) for modulation based, at least in part, on functional neuroimaging of the patient's brain or a combination of population data and functional neuroimaging of the patient's brain to determine a patient-specific brain network profile for the patient. Any suitable functional neuroimaging protocol may be used to elicit the brain network(s) underlying the patient's central nervous system condition. For example, neuroimaging data may be obtained for a patient during one or more conditions including, baseline conditions, (for example, during resting eyes-open, during resting eyes-closed), or during activation while engaged in a task including, but not limited to, an emotional task, a sensory task, a memory task, a stressor task, cognitive task, target detection task or other type of task which may activate the brain network underlying a characteristic of the central nervous system condition, or by comparing the resting and activated states. In some embodiments, imaging data may also be obtained for a patient while the patient is presented with stimuli to which a response may, or may not, be required, or using stimuli which have a low or high emotional aspect (e.g., faces with different expressions, unpleasant or disturbing images), or during activation with cues related to a disorder, such as displaying drug paraphernalia to a person with substance abuse disorder or phobic objects to one with a phobia. In some embodiments, patients may also be asked to internally generate stimuli (e.g., think of an unpleasant experience).

In some embodiments, imaging data may also be collected while the patient is exposed to a treatment medication, a substance which may acutely modify or worsen the brain disorder, or a substance which alters brain activity or metabolism in a useful manner with respect to gaining information about the brain network(s) underlying a characteristic of the disorder. Imaging data across conditions may be manipulated (e.g., subtracting a baseline condition from a task condition), processed, and analyzed any suitable technique, examples of which are known. The results of the neuroimaging may then be used to obtain information related to the brain network(s). Additionally, in some embodiments the patient neuroimaging data may be used to assist in determining the placement of the sensors and stimulators, and may be used to adjust both initial as well as subsequent parameters for neuromodulation, as discussed in more detail below.

Neuroimaging data collected from the patient may be processed using any suitable technique to derive information about the brain network(s) underlying the central nervous system condition. For example, brain network(s) may be identified using techniques including, but not limited to, structural equation modeling (SEM), dynamic causal modeling (DCM), and brain electrical source analysis (BESA), and correlation techniques, such as partial least squares (PLS), to process neuroimaging data for the patient. In some embodiments, a brain network for modulation may be identified as including the brain regions (e.g., reflected as imaged voxels of a neural region) which show covariance with a characteristic of the disorder. Covariance may be determined using any suitable statistical technique including, but not limited to, a seed PLS technique.

In some embodiments, one or more brain networks may be identified as circuits determined by correlating patient neuroimaging data with at least one characteristic of a mood, anxiety, or other psychiatric or neurological central nervous system condition. For example, brain network(s) may be identified as a set of putatively interacting structures which are inferred (e.g., by correlation) to contribute to a disease state or trait.

Continuing with the ADHD example above, given the strong association between an elevated TBR measurement and an ADHD diagnosis, in some embodiments the brain network(s) and/or brain region(s) may be identified based, at least in part, on QEEG data exhibiting elevated TBR. For example, the spatial distribution of TBR measurements across a plurality of EEG electrodes may be used to identify brain network(s) contributing to the elevated TBR measurements. In some embodiments, brain network(s) may be identified based, at least in part, on a comparison of the patient's EEG data to data obtained by clinical studies investigating ADHD brainwave activity or by a comparison to databases of normative brainwave activity.

The inventor has recognized that the relative contribution of excess theta activity versus depressed beta activity in patients with ADHD may vary considerably from patient to patient. Accordingly, in some embodiments, the brain network(s) for theta activity and for beta activity are considered as comprising separate networks. In such embodiments, the spatial distribution of theta brainwave activity and/or beta brainwave activity may be used to identify brain network(s) contributing to the elevated TBR measurements.

The abnormally high power of theta brainwave activity observed in patients with ADHD during the EO-RS condition is typically broadly distributed across all cortical structures with slightly higher values being observed in the midbrain region. When the brain is at rest, theta brainwaves are believed to connect the areas of the brain responsible for cognitive function to the Default Mode Network (DMN), which is a network of brain regions active when an individual is not focused on the outside world and the brain is at wakeful rest. In patients without ADHD, when the frontal regions of the brain become activated, the level of theta activity is reduced facilitating detachment from the DMN. However, in patients with ADHD, theta activity remains at high levels. The inability of the brain to detach from the Default Mode Network in patients with ADHD may be at least partly responsible for the hypo-activation of frontal brain regions observed in patients with ADHD.

The depressed levels of beta activity found in patients with ADHD are localized primarily in the frontal regions of the brain. Additionally, it has recently been shown that not only is the absolute power of beta brainwave activity reduced in patients with ADHD, but there is also a distinct right-lateralized shift in cortical activity as compared to patients without ADHD. The rightward shift is believed to be a compensatory mechanism for the reduced processing capabilities of the left hemisphere in patients with ADHD.

Beyond the anomalies found in the theta and beta frequency bands, differences between patients with and without ADHD have also been observed in the alpha brainwave frequency band. In ADHD, alpha activity in frontal brain regions has been found to be reduced, predominantly in the visual processing network. During periods of mental inactivity, alpha brainwaves are thought to exert an important inhibitory effect on irrelevant stimuli and, therefore, the weaker power of alpha activity in patients with ADHD may be responsible for the distractibility commonly observed in these patients.

Conversely, in patients without ADHD, when the frontal regions of the brain become activated, the level of alpha activity decreases, presumably permitting more efficient communication between cortical structures of the frontal lobe. However, in patients with ADHD, the power of alpha brainwave activity increases in response to frontal region activation. By inhibiting brainwave activity within the frontal cortex and between connecting structures, the increased alpha activity is believed to play a role in the hypo-activation that characterizes brain activity in patients with ADHD.

Accordingly, in some embodiments, brain network(s) underlying ADHD may be determined by comparing QEEG data from a patient in frequency bands other than theta and beta (e.g., alpha or gamma QEEG data) with population data from clinical studies examining brainwave activity in patients with and without ADHD. For example, a recent study measured the relative power of delta, theta, beta and alpha activity in three groupings of brain regions and found four clusters of brainwave activity identified as being specific to patients with ADHD. These were characterized by (a) elevated beta activity, (b) elevated theta activity with deficiencies of alpha and beta activity, (c) elevated slow wave activity with less fast wave activity, and (d) elevated alpha activity. Each cluster was found to be highly correlated with specific behavioral characteristics exhibited by ADHD patients. Accordingly, in some embodiments, behavioral data associated with a patient may be used to characterize the patient's behavior as belonging to one of these four (or some other number) of clusters of ADHD patients, each of which correlates with a particular ADHD brainwave activity signature. Additionally, a comparison between the patient's EEG data and the population data for the identified cluster's brainwave pattern may be used to identify additional brain network(s) and/or brain region(s) for treatment with neuromodulation using one or more of the techniques described herein.

In some embodiments, brain network(s) may be determined based, at least in part, on QEEG imaging data collected under certain task-related conditions. For example, it has been shown that, under dynamic conditions, brainwave activity in patients with ADHD differs markedly from that of patients without ADHD. Accordingly, QEEG data may be collected to investigate the patient's brainwave activity during a transition from an eyes-open, resting state (EO-RS) condition to a task-related condition. Non-limiting examples of task-related conditions include tests of executive function, such as the Go/No Go and Stroop tests, and tests of working memory, such as verbal n-back and Span Board tests. The recorded QEEG imaging data may be compared to normative data as described above to identify abnormal brainwave activity in brain network(s) and/or brain region(s). Such comparisons enable the identification of abnormal brainwave activity in neural network(s) and/or brain region(s) whose activity is dependent upon the activity in networks or regions connected to the abnormally performing network. Such activity may also be abnormal, or, it may be normal, but cause an abnormal functioning of the connected network.

As discussed above, some central nervous system disorders are associated with complex characteristics that may involve multiple different brain networks. Accordingly, the same neuromodulation therapy protocol may not be effective for all patients diagnosed with the same central nervous system condition. In some embodiments, a treatment protocol is defined for individual patients to provide targeted neuromodulation that attempts to differentially normalize, or otherwise modulate, each of the abnormal brain networks to treat one or more aspects of the condition manifested in the patient. In some embodiments treatment is guided not only by considering the level of activation in one or more brain regions, but also relative activation, compensatory mechanisms, and the normal/abnormal connectivity and interactions within the brain networks that underlie various characteristics of central nervous system conditions.

Returning to the process of FIG. 1, in act 104, a treatment plan is determined for a patient. The treatment plan may include one or more treatment protocols, each of which includes suitable information for treating at least one of the brain networks identified in act 102. In one embodiment, treatment protocols may be defined by medical personnel treating the patient based on the results of functional imaging showing regions of the network where brainwave activity is increased, decreased, or otherwise altered. As discussed above, the results of the functional imaging may be analyzed using path analysis or any other suitable analysis which provides a model of the brain network to modulate, and the treatment protocol may be iteratively adjusted until, for example, the model indicates that brain activity within the brain network is within a specified (e.g., normal) range.

In some embodiments, a treatment protocol is defined for each brain network to be treated and includes at least the following parameters: (1) brain region(s) to be modulated, (2) brainwave frequency band(s) within the brain region(s) to be modulated, (3) a desired outcome of the modulation, and (4) conditions under which the modulation is to take place. Each of these parameters is discussed in more detail below.

The brain region(s) to be modulated may be determined based, at least in part, on the brain network for which the treatment protocol is being defined. For example, the brain network may include multiple brain regions distributed throughout the brain and one or more of these multiple brain regions may be targeted for modulation. Some brain networks may only include a small number of brain regions (including only a single brain region), whereas other brain networks may include a large number of brain regions. The brain regions to be modulated may include all or a subset of the brain regions included in the brain network and may be selected based, at least in part, on the functions of each of the brain regions within the brain network. For example, if one or more of the brain regions are known to function as "core" brain regions within the brain network, the one or more core brain regions may be identified as the brain regions to be modulated.

Brain regions for modulation may be identified in any suitable way including, but not limited to, being identified based on knowledge gained from the patient or knowledge from population data. When population data is considered, the data may include models of the putative brain networks responsible for a particular brain condition and appropriate targets of the network may be identified prior to treatment based on the population data. A comparison of a model of the patient's brain networks to models of networks of patients for whom treatment was successful may also assist in designing a treatment protocol. Using data about one or more brain networks of the patient and some aspect of the patient's disorder, a relationship between the brain network(s) and the aspects of the disorder may be established using, for example, imaging techniques such as path/PLS analysis, SEM, or transfer entropy computations, as discussed above In some embodiments, brain regions for neuromodulation and/or candidate neurostimulation parameters may be determined using methods such as correlation of hyper- or hypo-activation with some aspect of the patient's condition, absolute or relative activation, connectivity (path) coefficients, directionality of influences within a network, latency differences between activation of different regions, or any other suitable aspect of the patient's condition. In some embodiments brain regions for modulation may be identified based on the brain region(s) that demonstrate the largest abnormal brainwave activity in one or more frequency bands compared to patients without the central nervous system condition. In some embodiments, the brain regions to be modulated may be identified based, at least in part, on functional neuroimaging data recorded while the patient is performing one or more tasks, as discussed above.

The brainwave frequency band(s) to be modulated may be determined based, at least in part, on characteristics of the central nervous system condition for which the patient has been diagnosed, brainwave activity determined from functional neuroimaging data collected from the patient, one or more behavioral characteristics of the patient, or any combination thereof. For example, as discussed above for the condition of ADHD, patients may be identified as being within one of a plurality of ADHD subgroups, each of which is characterized by abnormalities of brainwaves within different frequency bands, and the brainwave frequency band(s) to be modulated may be determined based, at least in part, on which subgroup the patient is associated with. In some embodiments, the treatment protocol may specify that only a single brainwave frequency band be modulated across all brain regions in the targeted brain network. In other embodiments, the treatment protocol may specify that multiple brainwave frequency bands be modulated in different brain regions of the targeted brain network. Any suitable type or combination of particular brainwave frequency bands may be specified in the treatment protocol for modulation, an example of which is discussed below for patients with ADHD.

A treatment protocol defined in accordance with the techniques described herein includes desired outcomes of the modulation, which may be used both to set the initial stimulation parameters and to determine whether the delivered neuromodulation treatment is effective. Furthermore, the desired outcomes may be specified for individual brain regions, for portions of the brain network, or for the brain network as a whole. As discussed in more detail below, an aspect of the neuromodulation techniques described herein is the ability to modulate brain activity in brain regions or brain networks in an informed way to provide therapy to remediate the abnormal activity in those brain regions/networks. The inventor has recognized that different modulation stimuli may be presented based on whether a particular brain region is identified as being hyperactive, hypoactive, or based on the synchronicity of neural activity within and/or between brain regions in a brain network. Accordingly, in some embodiments, the desired outcomes specify whether the effect of the modulation is to increase, decrease, synchronize, or desynchronize the brainwave activity in one or more brain regions of the brain network.

In some embodiments, a treatment protocol may also include desired outcomes based on a desired power of brainwave activity within a brain region and/or brain network to be modulated. For example, the desired outcome may specify that the power of brainwave activity within a brain region is to be increased or decreased by a particular amount in response to the modulation. Power of brainwave activity within a brain region and/or brain network may be determined in any suitable way, examples of which are known and will not be further described herein. Any other suitable measure quantifying brainwave activity within a brain region and/or brain network other than the power of brainwave activity with the brain region and/or brain network may additionally or alternatively be specified in a treatment protocol, and embodiments are not limited in this respect.

A treatment protocol designed in accordance with some embodiments may also specify the conditions under which the modulation is to take place. For example, the treatment protocol may specify the timing of providing the modulation. Examples of timings to provide the modulation include, but are not limited to, continuously, periodically, in response to a sensed data (e.g., the power level of the targeted brainwave activity being above or below a specified value), in response to specified brainwave activity being sensed in a connected brain network or brain region, in response to patient input, and in response to an external condition or event. For example, a criterion in a treatment protocol may specify that a first brain region must demonstrate an average value of a characteristic which is X % above that of second brain region (e.g., the brainwave activity observed in left frontal cortex must have 15% lower activity levels than the brainwave activity in right parietal cortex).

In some embodiments, treatment criteria may also be constrained by one or more conditional rules which govern the evaluation of sensed data. For example, a conditional rule may state that a network event must occur for at least a specified duration before a criterion is considered to have been satisfied. The treatment criteria based on sensed data with respect to brain networks may utilize comparisons with threshold values, statistical criteria, population or self-norm data, or any other suitable measure, and may rely upon the output of modeling algorithms which compare the results of modeling of the current data to target values for the model. Additionally, each treatment protocol in a treatment plan may be specified independently of other treatment protocols in the treatment plan to allow for different criteria to be set for different brain networks. In some embodiments, the criteria specified for one treatment protocol may depend, at least in part, on the output of another treatment protocol in the treatment plan.

As discussed above, some treatment protocols may specify that neurostimulation be performed in response to sensed medical events. A medical event may be detected, for example, using a template matching strategy or algorithm which produces a probability score that an event has occurred where, when the probability score is above a specified threshold, the event is considered to have occurred. Alternatively, a medical event sensing determination may provide a true/false indication that the event has occurred. Non-limiting examples of a medical event include a seizure, a network state, and an approximately simultaneous drop in activity at a number of sensors which reflects a change in the network state. The absence or presence of a medical event may be used to determine that a treatment criterion is satisfied, and embodiments are not limited in this respect.

Additionally, if stimulation was occurring before the medical event occurred, detection of the medical event may lead to a change in the stimulation protocol including the stimulation parameters, or the addition of a responsive stimulation protocol. Alternatively, if stimulation was not occurring prior to the detected medical event, the treatment protocol may specify that, in response to detection of a sensed medical event, stimulation should begin.

In an example of a treatment protocol which addresses compensating for abnormal connectivity, the activity of one region of a network may be used to guide the neurostimulation of at least a second region of the network. Rather than just increasing the activity of a second region of a network, the aim of the treatment protocol may be to correlate some aspect of the brain activity in the second region with the brain activity in the first region. By altering the firing patterns, activation levels, or other characteristics of brain activity in the second brain region of the network, the second brain region may become more or less receptive to input from the first region. Accordingly, stimulation provided to the second region drives, entrains, or primes the neural activity of the second region so that afferent input from the first region is enhanced. In this way, some embodiments use correlation analysis of data from brain networks to guide the development and modification of some treatment protocols, where the aim is not to increase or decrease the overall level of activity in a brain network, but rather to alter the timing and correlation, of activity between two or more brain regions of the brain network.

The inventor has recognized that designing a treatment protocol relying upon information about brain networks, rather than, or in addition to information about a patient's behavioral symptoms, may provide for more effective treatment of a central nervous system condition than relying on an analysis of behavioral symptoms alone. By evaluating the brain network of the individual, a direct measure of the pathology may be used to create an appropriate treatment protocol. For example, measures from a brain network of an individual may be statistically compared to different clusters in a database to classify the network of an individual into a particular subclass. An exemplary type of classification may be related to treatment successes, wherein different subclasses of networks which have been shown to improve (e.g., normalize) in response to modulation follows a particular treatment protocol created. Classification of a patient may guide the selection of the treatment protocol for that individual. As discussed above, selecting the number, location, and type of neuromodulation that may be successful in improving a brain network may be determined, at least in part, on evaluating brain network data for a patient. Consequently, the likelihood of providing successful therapy for the behavioral and cognitive symptoms of a disorder may be increased. In some embodiments a treatment protocol may be selected by sensing neuroimaging data, evaluating neuroimaging data to provide at least one measurement of a brain network, performing a comparison of the at least one measurement of a brain network to a database of two or more classes of brain networks, and selecting a treatment protocol based, at least in part, on the results of the comparison.

Returning to the example of ADHD discussed above, some patients with ADHD exhibit brainwave abnormalities in one or more of the theta, beta, and alpha frequency bands. A treatment protocol designed in accordance with the techniques described herein may include criteria to remediate the brainwave abnormalities in brain networks underlying ADHD.

The abnormally high power of theta brainwave activity frequently observed through QEEG imaging in patients with ADHD is often diffusely distributed across multiple brain regions. Additionally, in contrast to patients without ADHD whose theta brainwave activity typically does not vary significantly between eyes-closed, eyes-open, and task-related observations, theta brainwave activity in patients with ADHD has been found to increase from an eyes-open condition to a task-related condition. The magnitude of the difference in relative theta brainwave activity power between patients with ADHD and patients without ADHD is typically in the range of 25% to 35% as measured from baseline. An example treatment protocol for treating patients with ADHD may include parameters for targeting the abnormalities in theta brainwave activity. A desired objective in such a treatment protocol may be to reduce the overall power of theta brainwave activity by an amount that the patient's baseline value differs from age-matched normative values when measured at the Cz EEG electrode location during EO-RS conditions. The treatment protocol may further specify that all brain regions are to be modulated with an emphasis on modulating the midbrain region, and that the modulation is to be administered continuously.

The diminished level of beta brainwave activity frequently observed in patients with ADHD is often centered in the frontal and prefrontal cortices. In addition to the large difference between the relative power of beta activity between patients with and without ADHD which, in some studies, approaches 50%, recent studies have shown an abnormal bias in brainwave activity to the right hemisphere during cognitive and sensory related tasks, in contrast to a leftward bias in brainwave activity among patients without ADHD. The example treatment protocol may include parameters for targeting the abnormalities in beta brainwave activity. Desired objectives in the treatment protocol may include increasing the overall power of beta brainwave activity by an amount that the patient's baseline value differs from age-matched normative values when measured at the Cz EEG electrode location during EO-RS conditions, and shifting the distribution of beta brainwave activity between the right and left hemispheres to more closely match normative values. The treatment protocol may also specify that neuromodulation should be focused on frontal regions of the brain with an emphasis on modulating the left hemisphere frontal regions, and that the modulation is to be administered continuously.

Some patients with ADHD exhibit reduced alpha brainwave activity in the resting state compared to patients without ADHD, with the average difference being in the range of 20 to 25%. In response to activation of the frontal and visual cortexes, the power of alpha brainwave activity in patients with ADHD typically increases by 8-10%, especially in the posterior and midline frontal regions. In contrast, alpha brainwave activity in patients without ADHD often decreases by approximately the same magnitude in all areas of the brain. The example treatment protocol may include parameters for targeting the abnormalities in alpha brainwave activity. Desired objectives in the treatment protocol may include increasing the overall power of alpha brainwave activity by an amount that the patient's baseline value differs from age-matched normative values when measured at the Cz EEG electrode location during EO-RS conditions, and in response to sensed brainwave activity in the frontal region, reducing the increase in alpha brainwave power achieved using the modulation described above by an amount such that the power of the patient's alpha brainwave activity is similar to age-matched normative values when measured at the Cz EEG electrode location during task-related conditions.

The above-described example of a treatment protocol for treating brainwave abnormalities in patients with ADHD includes addressing abnormalities in three different frequency bands and several different brain regions. It should be appreciated that treatment protocols designed in accordance with the techniques described herein may target brainwave abnormalities in any number of frequency bands (including a single frequency band), and the complexity of the treatment protocol does not limit the application of the techniques described herein for using brain modulation to treat patients with central nervous system conditions.

To implement the treatment plan, a neuromodulation plan is developed in accordance with the techniques described herein. The neuromodulation plan comprises one or more neuromodulation protocols, each of which is designed to accomplish the objectives of a corresponding treatment protocol in the treatment plan for the patient. A neuromodulation protocol may include presenting a single stimulus or multiple stimuli. The neuromodulation protocol may specify one or more stimulus characteristics for each stimulus included in the protocol. In some embodiments, the stimulus characteristics include (1) waveform characteristics, (2) frequency characteristics, (3) sensory pathway characteristics, (4) timing characteristics, and (5) power characteristics. Examples of each of these characteristics is described in more detail below.

The waveform characteristics of the stimulus include, but are not limited to, whether the stimulus is periodic (e.g., sinusoidal, square wave) or aperiodic. In particular, in some embodiments, stochastic stimuli may be used to synchronize or desynchronize populations of neurons in one or more brain regions of a brain network. The presence of certain kinds of "noise" can enhance the detection and transmission of weak signals in nonlinear systems, such as the human nervous system, via a mechanism known as stochastic resonance (SR). The phenomenon of SR, which is counterintuitive given that noise is generally considered to interfere with perception, is based on the concept that the addition of an optimal amount of noise lowers the threshold of the system so that small signals or stimuli, which in a no-noise environment would not be discernible, are now apparent. Examples of a SR-related benefit are observed in the detection of sensory signals. For example, SR has been found in audition, vision, and touch, where stochastic noise improves sensory discriminability. Accordingly, in some embodiments, at least one stimulus included in a neuromodulation protocol has a stochastic waveform characteristic such that the at least one stochastic stimulus modulates the condition of at least one of the somatosensory, auditory, and visual sensory systems upon presentation to a patient.

Empirical evidence suggests that central information processing and cognitive performance are also facilitated by the addition of optimal amounts of random noise. For example, it has been demonstrated that the addition of auditory noise improves the speed of arithmetic computations and recall on visual memory tasks in patients with ADHD. SR may have several different beneficial modes of action in the brain. For example, stochastic signals may induce new, more ordered regimes in neural assemblies leading to the formation of more regular structures and improved synchrony. Additionally, stochastic signals may increase the degree of coherence and cause the amplification of weak signals when applied to brain networks. Furthermore, SR when applied to brain networks may enhance both the local neural synchronization responsible for initial stimulus processing and indexed by local changes in spectral power in various frequency bands, and stochastic phase locking between distant brain regions cooperating in a network to manage processing of the effects of external stimuli. These observations imply that SR-mediated neural synchronization is a general mechanism of brain functioning. Stated differently, stochastic signals may play a multifaceted role in enhancing the performance of various aspects of the central nervous system. To this end, some embodiments are directed to promoting beneficial neural oscillation through the addition of particular (e.g., optimal) amounts of external noise to the central nervous system using stochastic signals to improve cognitive performance.

SR is often quantified by plotting its effect on information transfer as a function of noise intensity. This relationship follows an inverted U-curve function, where performance peaks at a moderate noise level. That is, there is an optimal level of noise that is maximally beneficial for performance; whereas a less than optimal amount has a diminished effect and a larger than optimal amount attenuates performance. Therefore, through the mechanism of SR, it is possible to promote neural synchrony by the addition of beneficial amounts of noise, as discussed above. Additionally, by adding excessive amounts of noise, neural synchrony may be inhibited or destroyed. In some embodiments, at least one stimulus in a neuromodulation protocol may be configured to introduce greater than optimal amounts of external noise to the central nervous system to desynchronize neural oscillation in one or more brain networks as treatment for a central nervous system condition.

The frequency characteristics of the stimulus refer to the frequency bandwidth of the stimulus. As discussed above, abnormal brainwave activity in different frequency bands (e.g., alpha, beta, delta, gamma, theta) characterizes dysfunction in brain networks underlying central nervous system conditions such as ADHD. The frequency characteristics of a stimulus may be specified to provide a bandwidth-limited targeted stimulus to modulate brainwave activity in one or more brain regions of the brain network within desired frequency bands determined to be dysfunctional (e.g., hypo- or hyper-activated, synchronized, or desynchronized). For example, a bandwidth-limited stochastic stimulus may be used to selectively modulate brainwave activity within a particular frequency band. Such bandwidth-limited stimuli may provide therapeutic advantages over broadband stimuli (e.g., white noise) that do not target modulation of particular frequency bands. It should be appreciated that a neuromodulation protocol designed in accordance with the techniques described herein may include at least one bandwidth-limited stimulus. Some embodiments may include a neuromodulation protocol that includes only stimuli that are not bandwidth limited. For example, some embodiments may include a neuromodulation protocol that includes only broadband stimuli and/or single-frequency (e.g., sinusoidal) stimuli. Yet other embodiments may include a neuromodulation protocol that includes a mix of bandwidth-limited and non-bandwidth-limited stimuli.

The sensory pathway characteristics of a stimulus may include an identification of which sensory pathway or pathways the stimulus will be presented, and may be a function of the brain region to be modulated and/or the frequency or frequency band of the stimulus. Projections from the primary sensory cortices (e.g., auditory, visual, and somatosensory cortices) reach throughout the brain, reflecting their importance to the performance of cognitive and motor functions. Sensory stimuli have a profound effect on the excitation of diverse regions within the brain. For example, the dense interconnects of the sensory pathways with the regions and brain networks of the brain that underlie cognition and behavior give rise to a broadly distributed pattern of brainwave response to sensory stimuli. The characteristics and locations of these responses are dependent upon the frequency of the stimulus and the sensory pathway or, in the case of multi-modal presentation, pathways through which the stimulus is presented. Thus, by mapping the location, frequency and spectral power of the brainwave activity evoked by a range of sensory stimuli, it is possible to create a topographic representation of the brain's response to sensory stimuli. In some embodiments, the sensory pathway or pathways selected to deliver a neuromodulatory stimulus to best accomplish the objectives of a treatment protocol may be selected based, at least in part, on using such as topography.

Moreover, the auditory, visual and somatosensory pathways preferentially stimulate different cortical regions and give rise to synchronized neural oscillations between the stimulated cortices and to other structures within the brain. Accordingly, some embodiments are directed to selecting sensory pathways that take advantage of the differential effects that various sensory inputs have on cortical structures throughout the brain to modulate neural oscillation within the brain.

The sensory pathway characteristics of a stimulus may also include whether the stimulus is unimodal (e.g., visual only) or multi-modal (e.g., visual and auditory). In addition to being highly integrated with brain structures, clinical evidence suggests that the somatosensory, auditory and visual pathways are also tightly integrated with each other and that a stimulus presented through one sensory pathway can influence the performance or functioning of other sensory pathways. For example, when a bandwidth-limited stimulus in the theta range is presented simultaneously through the auditory and visual pathways, the evoked response in the mid-brain region is greater than the combined power of the two individual stimuli when presented separately. Conversely, when a bandwidth-limited stimulus in the alpha range is presented simultaneously through the auditory and visual pathways, the power of the evoked response in the mid-brain region is lower than if the stimulus had been presented solely via the auditory pathway. The interaction of multiple sensory stimuli presented simultaneously or at different timings in accordance with a neuromodulation protocol designed in accordance with the techniques described herein results in a highly configurable system that can target and remediate specific brainwave abnormalities underlying many central nervous system conditions.

The sensory pathway characteristics may also include an indication of whether a stimulus is to be presented to the left side, right side, or both sides of the body. For example, auditory stimuli may be presented in the right ear and/or the left ear, visual stimuli may be presented in the right eye and/or the left eye, and tactile stimuli may be presented to somatosensory systems on the right side and/or left side of the body. The spatial presentation of the stimulus may differentially effect how the brain is modulated based on the differences in neural projections throughout the sensory pathways. Additionally, in the case of a somatosensory stimulus, the location or locations on the body where the stimulus is provided and whether the stimulus is mechanical, electrical, or a combination of mechanical and electrical, may also be specified.

The timing characteristics of the stimulus may include, but are not limited to, whether the stimulus is to be presented continuously, intermittently based on a fixed or variable time schedule, simultaneously with, or in some other defined relationship to another stimulus specified in the neuromodulation protocol, or contingent upon a specified variable or condition that is sensed by, or provided to, the stimulation system. In some embodiments, the timing characteristics, frequency characteristics, and sensory presentation pathway of the stimuli may be selected to produce an interfering effect on brainwave activity beyond the SR effect, discussed above.

The treatment protocol for modulating a particular brain network may include timing parameters that can be used, at least in part, to determine the timing characteristics of the stimuli for a corresponding neuromodulation protocol. It should be appreciated that different stimuli may have the same timing characteristics or different timing characteristics, and embodiments are not limited in this respect. For example, a neuromodulation protocol may include the continuous presentation of a first stimulus and presentation of a second stimulus in response to an event occurring as detected by sensor input. Independent timing and control of sensory stimuli presented in accordance with a neuromodulation protocol designed based on the techniques described herein enables a highly flexible and powerful system for treating central nervous system disorders with complex and heterogeneous brain activity in distributed brain networks.

Power characteristics for a stimulus include, but are not limited to, the initial power of the stimulus (e.g., decibels, lumens, volts), how the initial power value is to be determined, and, in instances where the power of the stimulus changes during the neuromodulation protocol, how the new power level(s) of the stimulus is to be determined (e.g., based on sensor input or using some other technique).

Returning to the ADHD example discussed above, a neuromodulation plan may be defined to target the brainwave abnormalities in the theta, beta, and alpha frequency bands. For example, as discussed above, if a sensory stimulus having a frequency in the theta frequency band is presented to either the auditory or visual pathway, the stimulus is likely to evoke theta brainwave activity at power levels that differ from brain region to brain region and are dependent on whether the stimulus is auditory or visual. Further, if the same stimulus is presented simultaneously through both sensory pathways, the level of theta brainwave activity evoked by the combined stimulus is greater than that evoked by presentation through either sensory pathway alone. Furthermore, in some brain regions, the power level of the simultaneous presentation is greater than the simple summation of the power levels of the two stimuli. The synergistic effects of multi-sensory presentation can be observed throughout the brain, but are most prominent in the midbrain regions. Additionally, in patients without ADHD, the relative power of theta does not change appreciably from the EO-RS condition under task-related conditions.

With this background in mind, an exemplary neuromodulation protocol to achieve the treatment objective of the theta activity treatment protocol may include the following characteristics:

| Stimulus Characteristic | Value |
|---|---|
| Waveform | Stochastic (noise) |
| Frequency | Bandwidth-limited (4-7 Hz) |
| Sensory pathway | Simultaneous auditory and visual |
| Timing | Continuous with one or two stimulus power levels depending on observed theta brainwave activity |

| Stimulus Characteristic | Value |
|---|---|
| Power | Step 1: In an EO-RS condition, gradually increase power level of the stimulus while monitoring changes in theta brainwave activity at Cz. When the level of theta brainwave activity at Cz electrode reaches the target value specified in the treatment protocol, the stimulus power level is recorded. This becomes the initial stimulus power level for the neuromodulation protocol.<br>Step 2: Under task-related conditions, theta brainwave activity at Cz is observed. If the observed level of theta brainwave activity remains within the range specified in the treatment protocol, then no change is made in the power level of the stimulus.<br>If an unacceptable increase or decrease in theta activity is detected, the power level of the stimulus is adjusted to return the level of theta brainwave activity to the target value range of the treatment protocol. The stimulus power level is recorded and becomes the "contingent" stimulus power level that is administered in response to sensed task-related conditions under the neuromodulation protocol. |

By convention, the beta brainwave frequency band is subdivided into two ranges; Beta-1, composed of frequencies between 13-17 Hz, and Beta-2, composed of frequencies between 18-30 Hz. Beta-1 is often referred to as the "sensorimotor rhythm" due to its importance in the functioning of the motor system. Although not exclusively, the primary function of Beta-2 brainwave activity is believed to be the facilitation of inter-cortical communications in the frontal and parietal lobes.

Further, Beta-2 brainwaves are believed to play an important role in processing visual stimuli and modulating the brain's response to them. As a result, presentation of stimuli through the visual pathway typically has a greater effect on Beta-2 brainwave activity in the frontal lobe than either auditory or bi-sensory presentation.

With this background in mind, an exemplary neuromodulation protocol to achieve the treatment objective of the beta activity treatment protocol may include the following characteristics:

| Stimulus Characteristic | Value |
|---|---|
| Waveform | Stochastic (noise) |
| Frequency | Bandwidth-limited (18-30 Hz) |
| Sensory pathway | Right-field visual |
| Timing | Continuous with no change in stimulus power level |
| Power | In an EO-RS condition, gradually increase power level of the stimulus while monitoring changes in beta-2 brainwave activity at Cz. When level of beta-2 brainwave activity at the Cz electrode reaches the target value specified in the treatment protocol, the stimulus power level is recorded. This becomes the stimulus power level under the neuromodulation protocol. |

Alpha brainwave activity plays a dualistic role in regulating cognitive function. In the resting state, alpha brainwaves are thought to play an inhibitory role in preventing extraneous stimuli or sub-conscious thought from entering the conscious realm. However, during brain activation, alpha brainwaves are thought to facilitate communication between the frontal and posterior regions of the brain, especially signaling activity in the gamma frequency range.

In studies investigating the responses evoked by sensory stimuli in the alpha frequency range, it is been shown that when a stimulus having a frequency within the alpha band is presented through the auditory pathway, a higher level of alpha brainwave activity is generated in all brain regions compared to when the stimulus is presented through the visual pathway, or through both the visual and auditory pathways simultaneously.

With this background in mind, an exemplary neuromodulation protocol to achieve the treatment objective of the alpha activity treatment protocol may include the following characteristics:

| Stimulus Characteristic | Value |
|---|---|
| Waveform | Stochastic (noise) |
| Frequency | Bandwidth-limited (8-12 Hz) |
| Sensory pathway | Auditory |
| Timing | Continuous with an initial and contingent stimulus power level |
| Power | Step 1: In an EO-RS condition, gradually increase the power level of the stimulus while monitoring changes in alpha brainwave activity at Cz. When the level of alpha brainwave activity at Cz electrode reaches the target value specified in the treatment protocol, the stimulus power level is recorded. This becomes the initial stimulus power level under the neuromodulation protocol.<br>Step 2: Under task-related conditions, starting with the stimulus power level determined in Step 1, gradually adjust the power level while monitoring alpha brainwave activity at Cz. When the level of alpha brainwave activity at the Cz electrode reaches the target value specified in the treatment protocol, the stimulus power level is recorded and becomes the "contingent" stimulus power level that is administered in response to sensed task-related conditions under the neuromodulation protocol. |

As discussed above, a neuromodulation protocol may be developed for each corresponding treatment protocol in the treatment plan, and the collection of neuromodulation protocols may be compiled into a set of processor-executable instructions for controlling the delivery of the sensory stimuli to the patient via one or more brain neuromodulation devices (BNDs), non-limiting examples of which are discussed in more detail below.

In addition to compiling the instructions contained in the neuromodulation protocols, in some embodiments, conflicts between the neuromodulation protocols are identified prior to finalizing the neuromodulation plan. Given the complexity and dynamic nature of the brain and the neural networks that connect it, conflicts between neuromodulation protocols in a neuromodulation plan may be result from various factors. For example, two neuromodulation protocols may specify modulation of the same brain region, with a first protocol specifying that brainwave activity within a certain frequency band is to be increased in the brain region, while the second protocol specifies that brainwave activity within a different frequency band is to be inhibited in the brain region. The opposite intended effects of the two neuromodulation protocols with respect to modulating neural activity in the brain region, even with stimulation occurring in different frequency bands, may interact and may partially, or completely, diminish the intended treatment outcomes of the individual neuromodulation protocols. In accordance with some embodiments, one or more techniques may be used to resolve identified conflicts. Such techniques include, but are not limited to, dynamic network modeling, cross-frequency and phase-amplitude analysis, and any other suitable technique for developing a new joint neuromodulation protocol that accomplishes the objectives of the two individual neuromodulation protocols. If a detected conflict or conflicts cannot be resolved while preserving the objectives of the treatment plan, then one or more aspects of the treatment plan (e.g., one or more of the treatment objectives or treatment protocols) may be adjusted to resolve the conflict.

Returning to the process of FIG. 1, after the neuromodulation plan has been determined, the process proceeds to act 108, where the brain network(s) are modulated in accordance with the neuromodulation plan. Prior to initiating modulation, one or more BNDs are programmed with parameters of the neuromodulation plan and are configured with the necessary stimulation and sensing devices to implement the neuromodulation plan. Programming of the BND may happen in response to determining the neuromodulation plan or at any other suitable time. If necessary, programmed neurostimulation protocols may be adjusted based on patient requirements or input from medical practitioners treating the patients.

Figure 2:
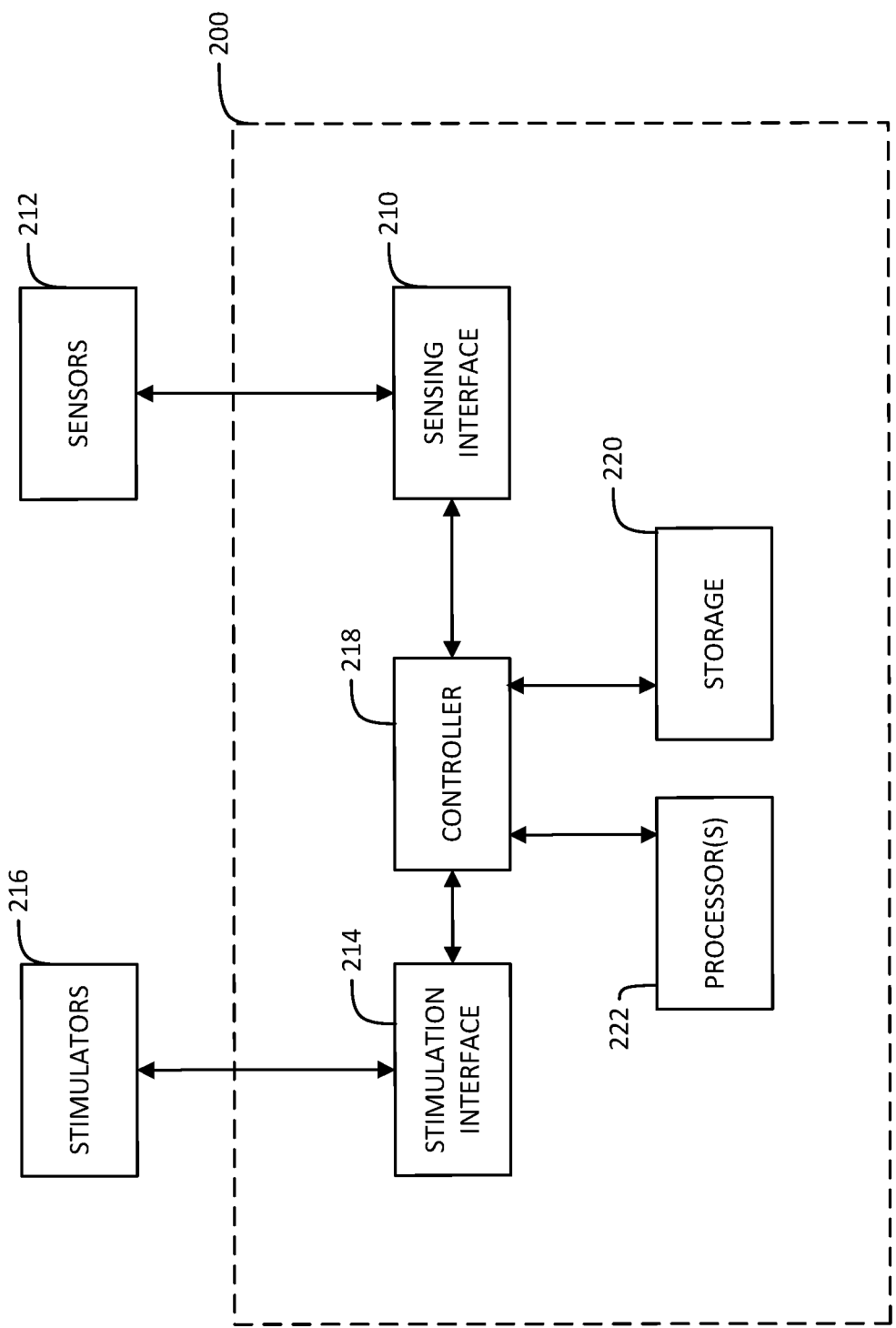
FIG. 2 is a schematic block diagram for a brain neuromodulation device (BND) that may be used in accordance with some embodiments.

FIG. 2 illustrates an illustrative brain neuromodulation device (BND) 200 that may be used in accordance with some embodiments to modulate one or more brain networks using the techniques described herein. BND 200 includes a sensing interface 210 configured to provide sensing operations and communications to sensors 212. Any suitable sensors 212 including, but not limited to, EEG sensors may be used in combination with BND 200 to provide sensing capabilities for sensing the effect of neuromodulation provided as a result of sensory instructions output from the BND. BND 200 also includes stimulation interface 214 configured to provide stimulating operations and communications to stimulators 216. Any suitable stimulators 216 including, but not limited to auditory stimulators, visual stimulators, tactile stimulators, mechanical stimulators, electrical stimulators, and magnetic stimulators, may be used in combination with BND 200 to provide sensory stimulation based on neuromodulation protocols stored by the BND.

BND 200 also includes controller 218 configured to communicate with sensing interface 210 and stimulation interface 214. For example, controller 218 may be configured to retrieve a neuromodulation protocol stored in storage 220 and determine stimulation parameters to transmit to stimulation interface 214. The retrieved neuromodulation protocol (or a corresponding treatment protocol also retrieved from storage 220) may specify sensor parameters indicating the sensor measurements of interest for the treatment plan. The sensor measurements may be transmitted from controller 218 to the sensing interface 210 to initialize and/or configure sensors 212 appropriately. In some embodiments, sensors 212 and/or stimulators 216 may be implemented as independent devices that include one or more power sources, one or more storage devices configured to store stimulation or sensing protocols, or any other suitable components that enable the devices to function properly without reliance on a centralized power source and/or processor.

In some embodiments, controller 218 comprises one or more of a power source (e.g., a rechargeable power source), at least one processor, memory, a real-time clock, and a communication interface to transmit instructions to stimulation interface 214 and sensing interface 210. BND 200 also includes one or more computer processors 222 configured to communicate with sensing interface 210 and/or stimulation interface 214 via controller 218. In some embodiments, processor(s) 222 may be configured to directly communicate with stimulation interface 214 and/or sensing interface 210 without communicating via controller 218.

Communication between the components of BND 200 may be implemented in any suitable way using one or more wired or wireless communications media. In some embodiments, processor(s) 222 may be configured to processes sensed data to produce result data, which is then used to determine if, and what type of, neuromodulation is needed.

In some embodiments, BND 200 may include additional circuitry (not shown) for processing the sensed data. For example, BND 200 may include circuitry for filtering, amplification/attenuation, A/D transformation, correlation, modeling, signal processing, registration, or any other suitable data processing function. Controller 218 may also be configured to enable BND 200 to initiate or modify neuromodulation based on, for example, pre-defined neuromodulation protocols, user input from an external controller, sensed data, result data, time of a real-time clock, patient input, contextual information about the salient aspects of an external environment that the brain is responding to, or any combination thereof. For example, in the case of contextual information, the power level and/or type of stimulus or stimuli that is optimally suited to provide effective treatment may differ depending on whether the performance of a task depends primarily on verbal memory/recall, arithmetic skills, impulse control, or some other type of task.

Processor(s) 222 may be programmed with executable instructions that, when executed by processor(s) 222 provides a treatment plan, as discussed above. In some embodiments, BND 200 comprises a wearable apparatus configured to modulate brain activity in response to real-time sensed data that enables the patient to receive neuromodulation outside of a clinical setting. For example, in some embodiments one or more components of BND may be implemented on a mobile device (e.g., a smartphone, tablet computer, smartwatch) such that patients with central nervous systems conditions may receive treatment while performing everyday activities outside of clinical or research setting.

Figure 3:
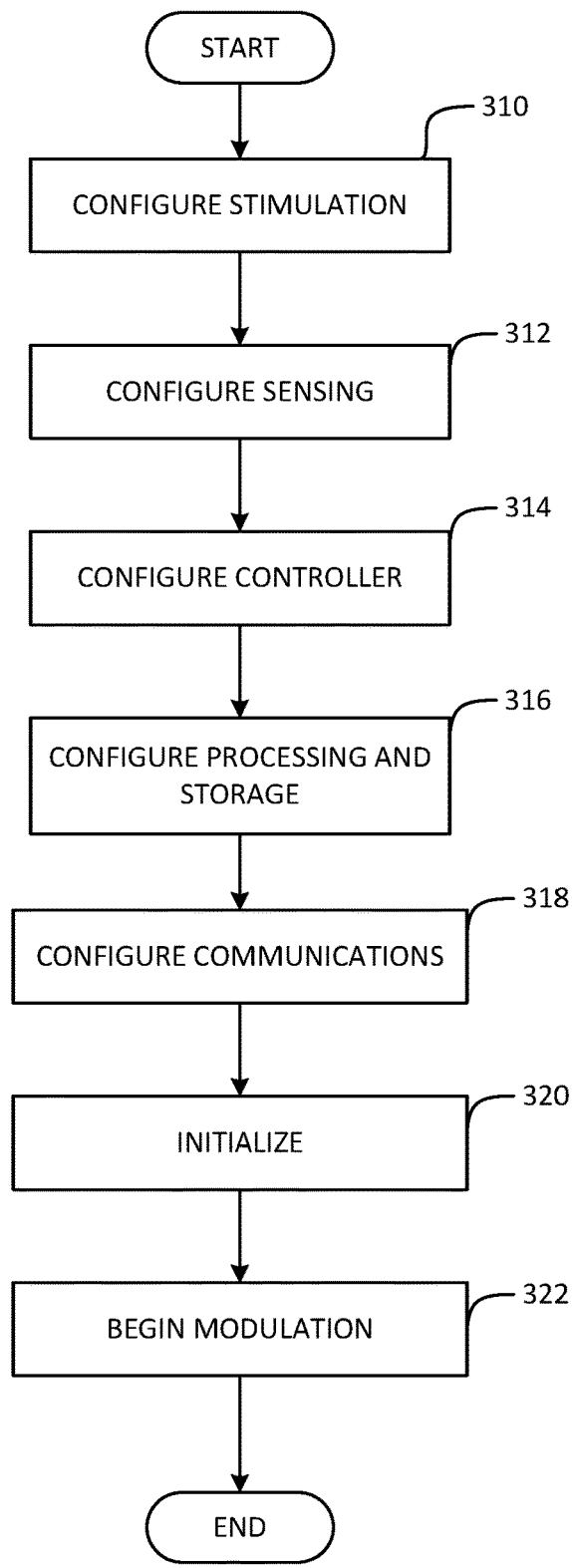
FIG. 3 is a flowchart of a process for configuring a BND to provide neuromodulation stimuli based on a neuromodulation protocol designed in accordance with some embodiments.

In some embodiments, BND 200 is configured with the ability to evaluate the sensed data using signal processing algorithms and/or modeling, and to compare the sensed data to stored treatment criteria defining normal or desirable values and ranges for the sensed data. FIG. 3 illustrates a process for configuring a BND to modulate brainwave activity in accordance with some embodiments. In act 310, the stimulation parameters of the BND are configured to accomplish a neuromodulation plan. In the illustrative example of the ADHD neuromodulation protocol discussed above, stimulators 216 may include an auditory stimulator and a visual stimulator, and the stimulators may be configured with appropriate stimulation parameters via stimulation interface 214.

Figure 5:
FIG. 5 is a bone conduction auditory device that may be used as a BND in accordance with some embodiments.

In some embodiments, the auditory and visual stimulators may be disposed on a single device, an example of which is shown in FIGS. 4A and 4B. FIG. 4A shows a pair of glasses with visual stimulators 410 arranged around the rims of the glasses. Alternatively, the BND may be configured to provide visual stimulations in other suitable way including, but not limited to, providing a heads-up display, providing the visual stimulation in the lenses of glasses, projecting visual stimulation directly onto the surface of a patient's retinas, or using any other suitable technique. FIG. 4B shows the arms of the glasses with an integrated bone-conducting auditory stimulator 420 configured to provide auditory stimulation. In other embodiments, the auditory stimulators and visual stimulators may be disposed on separate devices. For example, FIG. 5 illustrates a bone-conduction auditory stimulator. The auditory stimulator includes a controller and amplifier 510, a battery compartment 512, a power switch 514, a casing 516, a mechanical actuator (e.g., a piezo-actuator), an antenna and communications processor 522, and a patient input device. In some embodiments, patient input device 524 may not be needed if stimulation parameters are downloaded to the auditory stimulator from BND 200, as discussed above.

Figure 6:
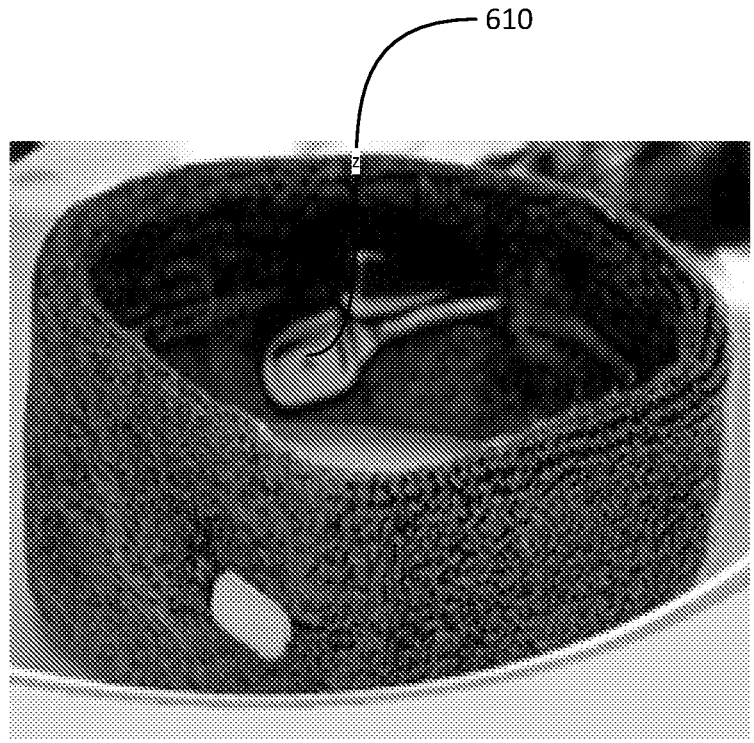
FIG. 6 is a mechanical/electrical stimulating device that may be used as a BND in accordance with some embodiments.

FIG. 6 illustrates a mechanical/electrical stimulating device that may be used in accordance with some embodiments. The mechanical/electrical stimulating device is configured as a wearable wristband and includes a mechanical/electrical stimulator 610 configured to provide sensory stimulation in response to instructions to do so.

Figure 7:
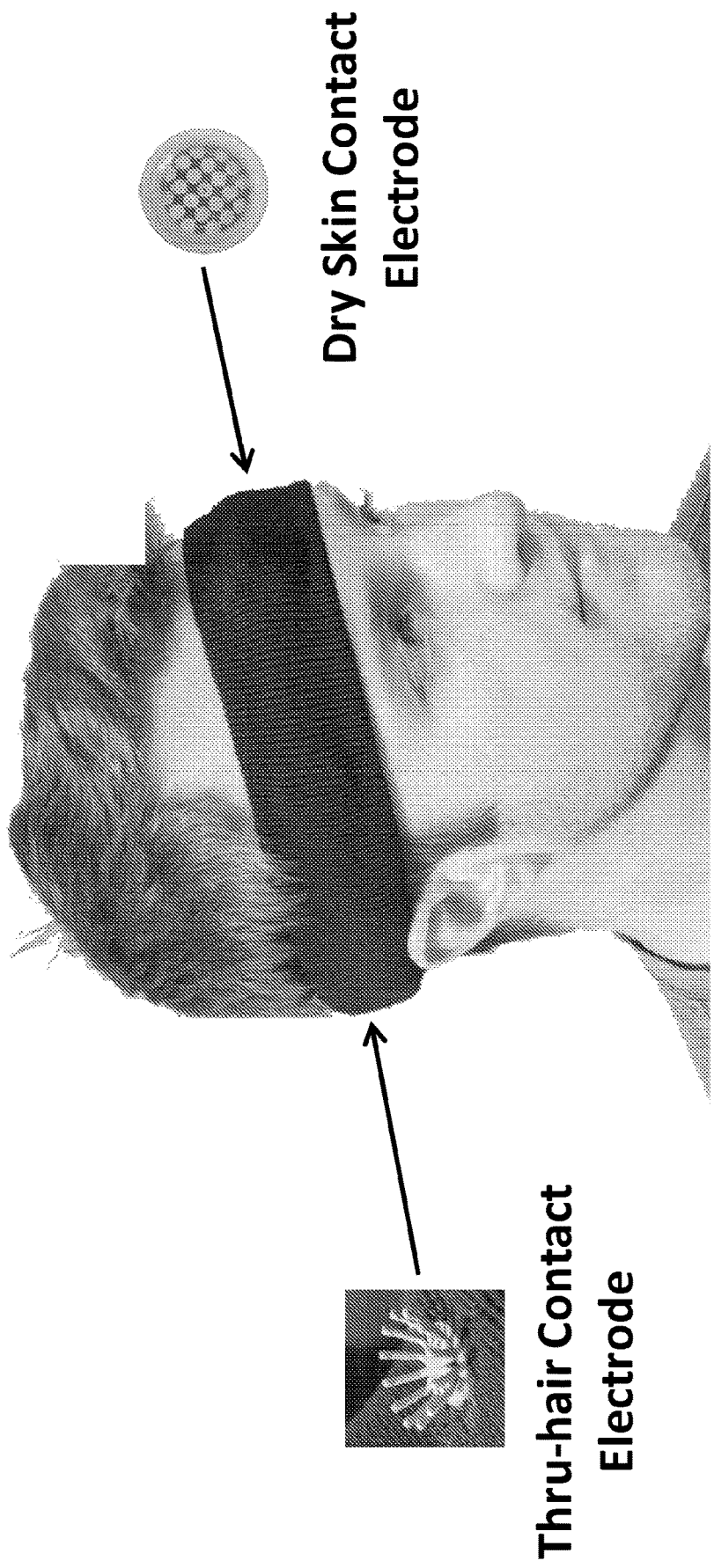
FIG. 7 is a wearable sensor device that may be used in accordance with some embodiments.

FIG. 7 illustrates a wearable sensor device configured to record sensor data (e.g., EEG data) that may be used in accordance with some embodiments. The sensor device is configured as a wearable headband, and includes a plurality of sensors for measuring EEG at multiple locations on the scalp. For example, as shown the sensor device includes dry skin contact electrode sensors and thru-hair contact electrode sensors. Any suitable type of sensor may alternatively be used, and embodiments are not limited in this respect.

The exemplary BND illustrated in FIGS. 4A and 4B combines auditory stimulators and visual stimulators in a single integrated and wearable device. It should be appreciated that BNDs designed for use with the neuromodulation techniques described herein may integrate one or more of auditory, visual, and tactile stimulators on the same device and/or within separate devices configured to communicate with one another using any suitable communications medium or media.

Figure 8:
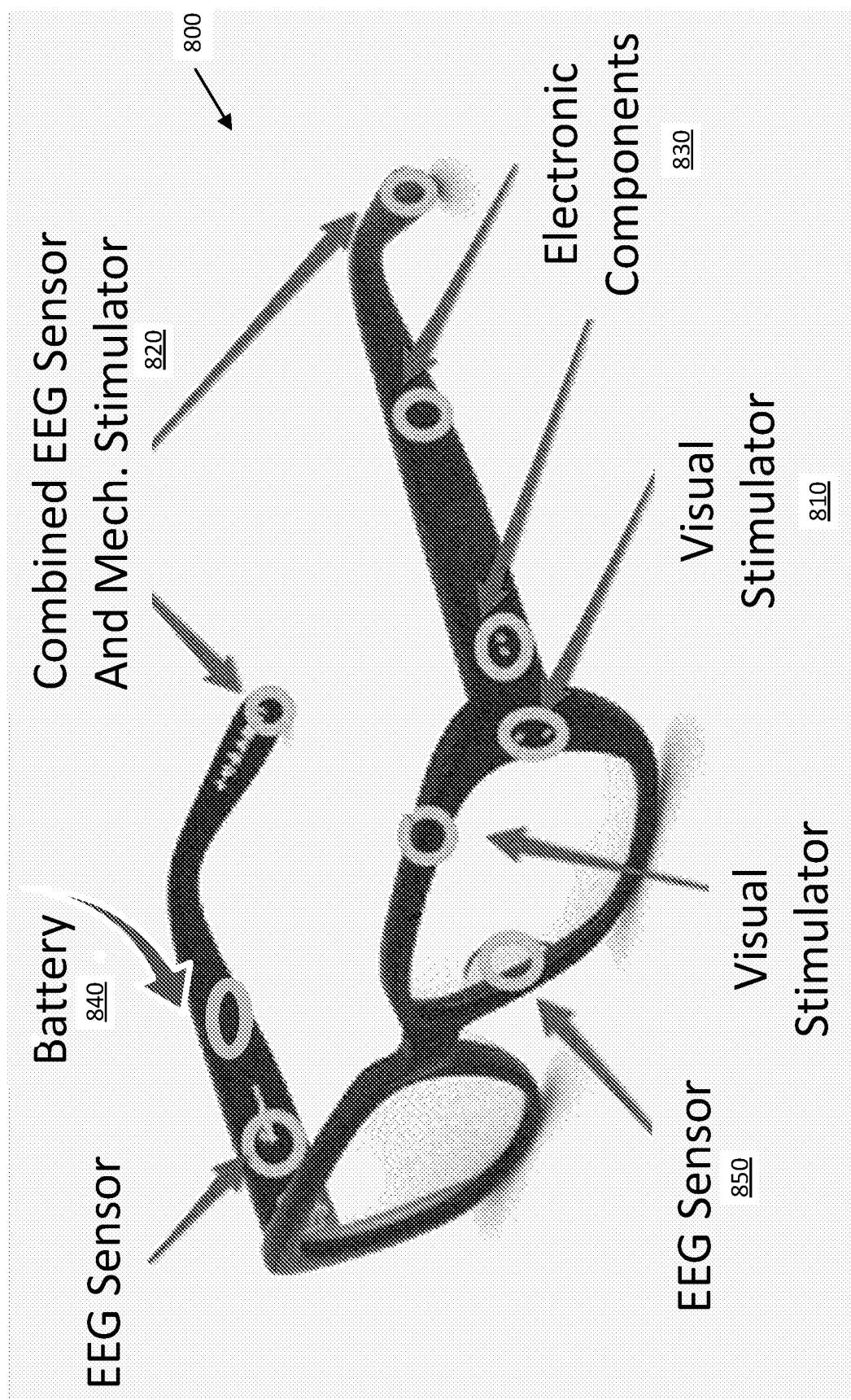
FIG. 8 is an example of a multimodal stimulation device with integrated sensors that may be used as a BND in accordance with some embodiments.

FIG. 8 illustrates a non-limiting example of a wearable multisensory stimulation device 800 that includes a sensing device integrated with multisensory stimulation capabilities that may be used in accordance with some embodiments. As shown, stimulation device 800 includes a plurality of visual stimulators 810, a plurality of mechanical stimulators 820, electronic components 830 (e.g., one or more processors), a battery 840, and a plurality of EEG sensor elements 850.

Returning to the process of FIG. 3, after configuring stimulation parameters, the process proceeds to act 312, where the sensing parameters are configured to detect the sensed data needed to accomplish one or more objectives in the treatment plan. In the illustrative example of ADHD, the sensed data relates to the activation level of the frontal lobe. As discussed above, in some embodiments the sensor data may be sensed using an EEG imaging device. In some embodiments, the EEG imaging device may be integrated with BND 200. In other embodiments, the EEG imaging device may be disposed in a device separate from but in communication with BND 200.

The process of FIG. 3 then proceeds to act 314, where the controller 218 of the BND is configured to provide instructions to the sensing interface 210 and stimulation interface 214 to accomplish the objectives of a neuromodulation protocol. Controller 218 may also be configured to communicate sensed data received from sensing interface 210 to processor(s) 222. In some embodiments, controller 218 is disposed on the same device as stimulation interface 214 and sensing interface 210, as shown in FIG. 2. Alternatively, controller 218 may be implemented on a device (e.g., a smartphone, laptop computer, smartwatch, or some other electronic device) separate from sensing interface 210, and stimulation interface 214 may be implemented, for example, as part of sensors 212 and stimulators 216, respectively. In such an implementation, controller 218 may be configured to communicate with sensing interface 210 and stimulation interface 214 using any suitable communication medium or media. In one implementation, Bluetooth or a similar data transfer technology may be used.

The process then proceeds to act 316, where the processing and storage is configured. In some embodiments, BND 200 includes a Processor and Data Storage Device (PDSD) configured to receive and store sensed data from controller 218. For example, as shown in FIG. 2, PDSD comprises storage 220 and processor(s) 222. Processor(s) may be configured to process the sensed data and configure other aspects of the BND based on external information including, but not limited to, patient information, and programming instructions communicated to the BND from an external device.

The process then proceeds to act 318, where the communications functionality of BND 200 is configured to provide communications between controller 218, PDSD, and one or more external devices configured to provide patient information, programming information, or any other information needed by BND to implement a treatment plan.

The process then proceeds to act 320, where the BND 200 is initialized to prepare the system for neuromodulation. The BND may be initialized in any suitable way, examples of which include programming the PDSD and controller 218 with information and instructions necessary to implement a neuromodulation protocol and providing and connecting the sensors 212 and stimulators 216 to the patient to enable these components to perform their intended functions. Initialization of the system may also include performing one or more safety checks and/or calibration to ensure that the BND will operate properly and safely.

Initialization may also include activing the BND and conducting a QEEG imaging study of the patient in the EO-RS condition to obtain a baseline EEG measurement in a manner similar to that used to develop one or more neuromodulation protocols, comparing the results of the baseline EEG measurement to target values specified in the neuromodulation protocol, and, if necessary, adjusting the stimulation parameters of the BND to accomplish the objectives of the programmed treatment plan. In some embodiments, initialization of the BND may also include activating the BND and conducting a QEEG imaging study of the patient in a task-related condition to obtain a baseline EEG measurement in a manner similar to that used to develop the neuromodulation protocol, comparing the results of the baseline EEG measurement to target values specified in the neuromodulation protocol, and, if necessary, adjusting the stimulation parameters of the BND to accomplish the objectives of the programmed treatment plan. Optionally, with the BND inactive, a baseline of the patient's cognitive and behavioral performance may be established using one or more psychometric tests.

After the baseline measurements have been made and the BND has been initialized, the process of FIG. 3 proceeds to act 322, where modulation begins in accordance with the programmed stimulus and sensing parameters for the neuromodulation protocol.

Returning to the process of FIG. 1, after modulation of the brain network(s) is performed for a particular amount of time, the process proceeds to act 110, where it is determined whether the treatment is effective. In some embodiments, determining whether the treatment is effective comprises determining whether sensed data meets one or more treatment objectives (e.g., whether the sensed data indicates that abnormal brainwave activity has been modulated so as to achieve desired levels of brainwave activity that are within a normative range). If it is determined that the treatment is effective, the stimulation parameters may not be changed and the process proceeds to act 112, where modulation continues until it is determined that treatment is no longer needed in act 112, or that the treatment is no longer effective in act 110.

If it is determined in act 110 that the treatment is not effective (e.g., when the sensed data fails to satisfy one or more treatment objectives, one or more stimulation parameters may be adjusted. In some embodiments, the treatment protocol may dictate that a treatment objective must fail to be met a threshold number of times, for a specified duration, to a specified degree, or using some other measure, before it is determined that the treatment is not effective and the stimulation parameters should be changed. To facilitate this analysis based on the treatment protocol, a history of comparison results, sensed data, or summaries of sensed data may be stored in storage 220, and controller 218 and/or processor(s) 222 may be programmed to evaluate this history, for example, by comparing the history of measurements to treatment criteria related to number of events of duration of the events, self-norms, or trends.

The treatment plan may include a control protocol which directs the controller 218 to control the treatment according to whether the treatment objectives are met or not, in relation to one or more programmed rules. For example, the treatment objectives may require that data sensed from two brain regions of a brain network each meet specified criteria, which may be set in relation to each other. The treatment criteria may be selected by the controller 218 from storage 220 which, in some embodiments, may be configured to store values related to the sensed data, self-norms, population norms, one or more rules, and other information and reference values utilized by the controller 218 during the sensing, stimulation, and evaluation processes carried out to provide the intended neuromodulation of the brain network. Historical records of sensed data itself and transformations and summaries of the sensed data, may also be stored in storage 220 of the BND. Storage 220 may be configured to store normative values of, for example, relative activity levels between structures. Storage 220 may also be configured to store stimulation protocols, including protocols to deter adaptation by the network to treatment stimulation which include, alternating different parts of the network. Adaptation-related stimulation protocols may be specifically triggered when adaptation, such as network adaptation, is detected by the BND.

With respect to determining whether the treatment is effective, evaluation may occur by comparing sensed data to reference data, which can be normative data, with respect to treatment criteria. In some embodiments, treatment failure may occur when brain activity of certain regions in the patient's brain deviate from the normative goals embodied by the treatment criteria, and treatment success may be judged by the return of the deviant features to within the normative range. Such changes may be quantified by representing the patient's brain state as a multivariate vector (e.g., a Brain State Vector (BSV)) in a multi-dimensional signal space using the length of the BSV to quantify the distance from the normative region centered around the origin of the signal space, or using any other suitable technique. The BSV may be a vector computed as the difference between a normative vector and an abnormal vector, or alternatively the BSV may be computed from z-scores and thus can be both statistically-based and normalized. Effective treatments may shorten the BSV, incorrect treatment may lengthen the BSV, and "side effects" may cause a change or rotation in the direction of the BSV in the signal space. The BSV can be computed upon the components of network model (e.g. SEM) wherein selected components best reflect the state of the disorder being treated. Stated differently, abnormal activity of the brain network may be normalized or changed to bring an undesirable characteristic of the network closer to a desired level.

In one embodiment, if the desired changes are not reflected in either the subjective experience of the patient, or the data sensed by the sensors, one or more of the modulated brain regions may be changed and/or an additional neuromodulation target may be selected. However, it should be noted that alterations of neural firing patterns and adjustments in neurotransmitter and receptor systems, which may play important roles in the therapeutic effects of brain stimulation, may have slow time courses, evolving over days or weeks, and accordingly evaluation of treatment efficacy may not be possible during the early stages of treatment. For example, stimulation may not immediately manifest therapeutic benefit. Furthermore, initial stimulation and/or sensing parameters may have to be altered should adaptation occur as neurostimulation continues over time.

Evaluation of sensed data may indicate that stimulation of two or more brain regions of a brain network does not meet a treatment criterion. A treatment criterion can be, for example, that some characteristic of neural activity (e.g., power in a certain frequency band, neurotransmitter levels) must remain above or below, a specified value. For example, evaluation of sensed data may indicate that stimulation of a neural target may not have reached treatment criteria for one or more regions of a brain network. Sensed data may relate, for example, to one or more of dopamine, serotonin, GABA or other neurotransmitter level, electrical activity of a neural population or group of cells (e.g., as sensed by EEG), or some other suitable sensed data such as the relative levels of one or more measurements made, either within, across, or between brain regions, or can relate to a change in these levels over time.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general-purpose hardware (e.g., one or more processors) that is programmed using microcode or software to perform the functions recited above.

In this respect, it should be appreciated that one implementation of the embodiments of the present invention comprises at least one non-transitory computer-readable storage medium (e.g., a computer memory, a USB drive, a flash memory, a compact disk, a tape, etc.) encoded with a computer program (i.e., a plurality of instructions), which, when executed on a processor, performs the above-discussed functions of the embodiments. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc. to modify elements does not by itself connote any priority, precedence, or order of one element over another or the temporal order in which acts of a method are performed. Such terms are used merely as labels to distinguish one element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

The invention claimed is:

1. A wearable neuromodulation device, comprising:
   at least one stimulator configured to output a bandwidth-limited sensory stimulus to a sensory organ of a user of the wearable neuromodulation device in accordance with stimulation parameters included in a neuromodulation protocol, wherein the bandwidth-limited sensory stimulus is configured to stimulate sensory neurons in the sensory organ, the sensory organ forming part of a sensory pathway, the sensory pathway being an auditory pathway, a visual pathway or a somatosensory pathway, the sensory pathway being connected to one or more brain regions in one or more brain networks of the user, thereby modulating neural activity within a brainwave frequency band or bands; and
   controller circuitry configured to:
       transmit the stimulation parameters to the at least one stimulator in accordance with the neuromodulation protocol to provide neuromodulation of the one or more brain regions in the one or more brain networks;
       receive input data representing performance of a task by the user of the wearable neuromodulation device following stimulation of the sensory organ with the bandwidth-limited sensory stimulus; and
       adjust, during operation of the wearable neuromodulation device, the stimulation parameters transmitted to the at least one stimulator based, at least in part, on the received input data.

2. The wearable neuromodulation device of claim 1, further comprising:
   at least one sensor configured to sense an effect of the neuromodulation, wherein adjusting the stimulation parameters transmitted to the at least one stimulator is further based, at least in part, on the effect of the neuromodulation sensed by the at least one sensor.

3. The wearable neuromodulation device of claim 2, wherein the at least one sensor is configured to sense the effect of the neuromodulation during operation of the wearable neuromodulation device.

4. The wearable neuromodulation device of claim 2, wherein the controller circuitry is further configured to compare the effect of the neuromodulation sensed by the at least one sensor to at least one target value, and wherein adjusting the stimulation parameters comprises adjusting the stimulation parameters based, at least in part, on the comparison of the effect of the neuromodulation sensed by the at least one sensor and the at least one target value.

5. The wearable neuromodulation device of claim 2, wherein the controller circuitry is further configured to:
   determine, based on the neuromodulation protocol, sensor information; and
   transmit the sensor information to the at least one sensor to initialize and/or configure the at least one sensor prior to stimulation with the wearable neuromodulation device.

6. The wearable neuromodulation device of claim 5, wherein initializing the at least one sensor comprises recording a baseline sensor measurement and providing the baseline sensor measurement to the controller circuitry, wherein the controller circuitry is further configured to adjust the stimulation parameters specified in the neuromodulation protocol based, at least in part, on the baseline sensor measurement.

7. The wearable neuromodulation device of claim 1, wherein the at least one stimulator includes a first stimulator configured to output a first bandwidth-limited sensory stimulus and a second stimulator configured to output a second bandwidth-limited sensory stimulus having at least one characteristic different from the first bandwidth-limited sensory stimulus.

8. The wearable neuromodulation device of claim 7, wherein the first bandwidth-limited sensory stimulus is configured to be output to a first sensory organ, and the second bandwidth-limited sensory stimulus is configured to be output to a second sensory organ.

9. The wearable neuromodulation device of claim 7, wherein each of the first bandwidth-limited sensory stimulus and the second bandwidth-limited sensory stimulus is a stochastic stimulus.

10. The wearable neuromodulation device of claim 1, wherein the neuromodulation protocol identifies the one or more brain regions to be modulated, one or more brainwave frequency bands within the one or more brain regions to be modulated, a desired outcome of the modulation, and one or more conditions under which the modulation is to take place.

11. The wearable neuromodulation device of claim 1, wherein the bandwidth-limited sensory stimulus is configured to inhibit and/or desynchronize neural oscillations in at least one of the one or more of the brain regions in the one or more networks.

12. The wearable neuromodulation device of claim 1, wherein adjusting the stimulus parameters comprises modifying the bandwidth-limited sensory stimulus to modulate a particular brainwave frequency band or bands within which neural activity is modulated.

13. The wearable neuromodulation device of claim 1, wherein the stimulation parameters include timing parameters for the bandwidth-limited sensory stimulus.

14. The wearable neuromodulation device of claim 13, wherein the timing parameters indicate whether the bandwidth-limited sensory stimulus is to be presented continuously, intermittently, or in response to the occurrence of a condition.

15. The wearable neuromodulation device of claim 1, wherein the neuromodulation protocol is selected based, at least in part, on health information about the user, wherein the health information relates to a disorder associated with the user, wherein the disorder is selected from the group consisting of a thought process disorder, a memory disorder, a mental disorder, an age-related disorder, a cognitive disorder, a motor disorder, and a sensory disorder.

16. The wearable neuromodulation device of claim 1, wherein the controller circuitry is further configured to initiate transmission of the stimulation parameters to the at least one stimulator or adjust the stimulation parameters in response to input from the user of the wearable neuromodulation device.

17. The wearable neuromodulation device of claim 1, wherein the controller circuitry is further configured to initiate transmission of the stimulation parameters to the at least one stimulator or adjust the stimulation parameters in response to contextual information about the environment of the user.

18. The wearable neuromodulation device of claim 1, wherein the at least one stimulator comprises an auditory stimulator configured to output the bandwidth-limited sensory stimulus to an auditory sensory organ.

19. The wearable neuromodulation device of claim 18, wherein the at least one stimulator further comprises a visual stimulator, and wherein the auditory stimulator and the visual stimulator are integrated on a single wearable neuromodulation device.

20. The wearable neuromodulation device of claim 1, wherein the task is performed by the user during stimulation of the sensory organ with the bandwidth-limited sensory stimulus.

21. A method of providing neuromodulation using a wearable neuromodulation device, the method comprising:
receiving a neuromodulation protocol including stimulation parameters;
transmitting the stimulation parameters to at least one stimulator in accordance with the neuromodulation protocol;
outputting, by the at least one stimulator, a bandwidth-limited sensory stimulus to a sensory organ of a user of the wearable neuromodulation device in accordance with the stimulation parameters to provide neuromodulation of one or more brain regions in one or more brain networks, wherein the bandwidth-limited sensory stimulus is configured to stimulate sensory neurons in the sensory organ, the sensory organ forming part of a sensory pathway, the sensory pathway being an auditory pathway, a visual pathway or a somatosensory pathway, the sensory pathway being connected to the one or more brain regions in the one or more brain networks of the user, thereby modulating neural activity within a brainwave frequency band or bands;
receive input data representing performance of a task by the user of the wearable neuromodulation device following stimulation of the sensory organ with the bandwidth-limited sensory stimulus; and
adjusting, during operation of the wearable neuromodulation device, the stimulation parameters transmitted to the at least one stimulator based, at least in part, on the received input data.

22. The method of claim 21, further comprising sensing an effect of the neuromodulation using at least one sensor, and wherein adjusting the stimulation parameters transmitted to the at least one stimulator is further based, at least in part, on the effect of the neuromodulation sensed by the at least one sensor.

23. The method of claim 22, wherein sensing the effect of the neuromodulation comprises sensing the effect of the neuromodulation during operation of the wearable neuromodulation device.

24. The method of claim 22, further comprising comparing the effect of neuromodulation sensed by the at least one sensor to at least one target value, and wherein adjusting the stimulation parameters comprises adjusting the stimulation parameters based, at least in part, on the comparison of the effect of neuromodulation sensed by the at least one sensor and the at least one target value.

25. The method of claim 22, further comprising transmitting sensor information indicated in the neuromodulation protocol to the at least one sensor to initialize and/or configure the at least one sensor prior to operation of the wearable neuromodulation device.

26. The method of claim 25, wherein initializing the at least one sensor comprises recording a baseline sensor measurement, and wherein adjusting the stimulation parameters comprises adjusting the stimulation parameters based, at least in part, on the baseline sensor measurement.

27. The method of claim 21, wherein the at least one stimulator includes a first stimulator configured to output a first bandwidth-limited sensory stimulus and a second stimulator configured to output a second bandwidth-limited sensory stimulus having at least one characteristic different from the first bandwidth-limited sensory stimulus.

28. The method of claim 27, wherein the first bandwidth-limited sensory stimulus is configured to be output to a first sensory organ and the second bandwidth-limited sensory stimulus is configured to be output to a second sensory organ.

29. The method of claim 27, wherein each of the first bandwidth-limited sensory stimulus and the second bandwidth-limited sensory stimulus is a stochastic stimulus.

30. The method of claim 21, wherein the neuromodulation protocol identifies the one or more brain regions to be modulated, one or more brainwave frequency bands within the one or more brain regions to be modulated, a desired outcome of the modulation, and one or more conditions under which the modulation is to take place.

31. The method of claim 21, wherein the bandwidth-limited sensory stimulus is configured to inhibit and/or desynchronize neural oscillations in at least one of the one or more brain regions in the one or more networks.

32. The method of claim 21, wherein adjusting the stimulus parameters comprises modifying the bandwidth-limited sensory stimulus to modulate a particular brainwave frequency band or bands within which neural activity is modulated.

33. The method of claim 21, wherein the stimulation parameters include timing parameters for the bandwidth-limited sensory stimulus.

34. The method of claim 33, wherein the timing parameters indicate whether the bandwidth-limited sensory stimulus is to be presented continuously, intermittently, or in response to the occurrence of a condition.

35. The method of claim 21, further comprising selecting the neuromodulation protocol based, at least in part, on health information about the user, wherein the health information relates to a disorder associated with the user, wherein the disorder is selected from the group consisting of a thought process disorder, a memory disorder, a mental disorder, an age-related disorder, a cognitive disorder, a motor disorder, and a sensory disorder.

36. The method of claim 21, further comprising initiating transmission of the stimulation parameters to the at least one stimulator or adjusting the stimulation parameters in response to input from the user of the wearable neuromodulation device.

37. The method of claim 21, further comprising initiating transmission of the stimulation parameters to the at least one stimulator or adjusting the stimulation parameters in response to contextual information about the environment of the user.

38. The method of claim 21, wherein the task is performed by the user during stimulation of the sensory organ with the bandwidth-limited sensory stimulus.

39. A wearable integrated neuromodulation device comprising:

at least one stimulator configured to output a bandwidth-limited sensory stimulus to a sensory organ of a user of the wearable integrated neuromodulation device in accordance with stimulation parameters, wherein the bandwidth-limited sensory stimulus is configured to stimulate sensory neurons in the sensory organ, the sensory organ forming part of a sensory pathway, the sensory pathway being an auditory pathway, a visual pathway or a somatosensory pathway, the sensory pathway being connected to one or more brain regions in one or more brain networks of the user, thereby modulating neural activity within a brainwave frequency band or bands;

at least one power source configured to provide operating power to at least one of the at least one stimulator and at least one sensor; and controller circuitry configured to:

transmit the stimulation parameters to the at least one stimulator in accordance with the neuromodulation protocol to provide neuromodulation of the one or more brain regions in the one or more brain networks;

receive input data representing performance of a task by the user of the wearable neuromodulation device following stimulation of the sensory organ with the bandwidth-limited sensory stimulus; and adjust, during operation of the wearable integrated neuromodulation device, the stimulation parameters transmitted to the at least one stimulator based, at least in part, on the received input data.

* * * * *